(12) United States Patent
Korth et al.

(10) Patent No.: US 7,518,009 B2
(45) Date of Patent: Apr. 14, 2009

(54) PROCESS FOR PREPARING MERCAPTOORGANYL (ALKOXYSILANES)

(75) Inventors: Karsten Korth, Grenzach-Wyhlen (DE); Dorit Wolf, Oberursel (DE); Steffen Seebald, Kahl am Main (DE); Philipp Albert, Lorrach (DE); Reimund Pieter, Bensheim (DE); Alfred Alig, Geiselbach-Omersbach (DE)

(73) Assignee: Evonik Degussa GmbH, Essen (DE)

( * ) Notice: Subject to any disclaimer, the term of this patent is extended or adjusted under 35 U.S.C. 154(b) by 240 days.

(21) Appl. No.: 11/415,183

(22) Filed: May 2, 2006

(65) Prior Publication Data

US 2006/0252952 A1    Nov. 9, 2006

(30) Foreign Application Priority Data

May 3, 2005    (DE) .................... 10 2005 020 535

(51) Int. Cl.
  *C07F 7/08* (2006.01)
  *C07F 7/18* (2006.01)
(52) U.S. Cl. .................................... 556/427
(58) Field of Classification Search ................ 556/627, 556/427
See application file for complete search history.

(56) References Cited

U.S. PATENT DOCUMENTS

| | | | |
|---|---|---|---|
| 3,350,345 A | 10/1967 | Vanderbilt | |
| 3,590,065 A | 6/1971 | Rakus | |
| 3,842,111 A | 10/1974 | Meyer-Simon | |
| 3,873,489 A | 3/1975 | Thurn | |
| 3,978,103 A | 8/1976 | Thurn | |
| 3,997,356 A | 12/1976 | Thurn | |
| 4,048,206 A | 9/1977 | Voronkov | |
| 4,076,550 A | 2/1978 | Thurn | |
| 4,153,063 A | 5/1979 | Roselius | |
| 4,456,718 A | 6/1984 | Brinkmann | |
| 4,514,231 A | 4/1985 | Kerner | |
| 4,551,541 A | 11/1985 | Hanisch | |
| 4,798,878 A | 1/1989 | Brinkmann | |
| 5,107,009 A | 4/1992 | Rauleder | |
| 5,637,209 A | 6/1997 | Wright | |
| 5,736,484 A | 4/1998 | Polanek et al. | |
| 5,780,538 A | 7/1998 | Cohen | |
| 5,840,952 A | 11/1998 | Kudo | |
| 5,859,275 A | 1/1999 | Munzenberg | |
| 5,914,364 A | 6/1999 | Cohen | |
| 5,977,225 A | 11/1999 | Scholl | |
| 6,133,466 A | 10/2000 | Edelmann | |
| 6,140,393 A | 10/2000 | Bomal | |
| 6,331,605 B1 | 12/2001 | Lunginsland | |
| 6,362,253 B1 | 3/2002 | Durel | |
| 6,403,228 B1 | 6/2002 | Mack | |
| 6,433,206 B1 | 8/2002 | Gedon et al. | |
| 6,465,544 B1 | 10/2002 | Bomal | |
| 6,465,672 B2 | 10/2002 | Rudolf | |
| 6,518,335 B2 | 2/2003 | Reedy | |
| 6,548,594 B2 | 4/2003 | Luginsland | |
| 6,849,754 B2 | 2/2005 | Deschler | |
| 6,893,495 B2 | 5/2005 | Korth | |
| 6,995,280 B2 | 2/2006 | Korth et al. | |
| 7,019,160 B2 | 3/2006 | Korth et al. | |
| 7,186,768 B2 | 3/2007 | Korth | |
| 7,332,619 B2 | 2/2008 | Korth | |
| 7,339,067 B2 | 3/2008 | Korth | |
| 7,384,997 B2 | 6/2008 | Hasse | |
| 2003/0083516 A1 | 5/2003 | Korth | |
| 2003/0130535 A1 | 7/2003 | Deschler et al. | |
| 2003/0200900 A1 | 10/2003 | Korth | |
| 2004/0266968 A1 | 12/2004 | Korth | |
| 2005/0124740 A1 | 6/2005 | Klockmann | |
| 2005/0124821 A1 | 6/2005 | Korth | |
| 2005/0124822 A1 | 6/2005 | Korth | |
| 2006/0052621 A1 | 3/2006 | Korth et al. | |
| 2006/0052622 A1 | 3/2006 | Korth et al. | |
| 2006/0161015 A1 | 7/2006 | Klockmann | |
| 2006/0204422 A1 | 9/2006 | Korth | |
| 2006/0241224 A1 | 10/2006 | Krafczyk | |

(Continued)

FOREIGN PATENT DOCUMENTS

DE    915334 C    7/1954

(Continued)

OTHER PUBLICATIONS

Dreschler, et al., "3-Chloropropyltrialkoxysilanes: Key Intermediates for the Commercial Production of Organofunctionalized Silanes and Polysiloxanes," *Agnew. Chem. Int. Ed. Engl.* 25:236-252 (1986).

(Continued)

*Primary Examiner*—Elvis O Price
(74) *Attorney, Agent, or Firm*—Michael A. Sanzo; Law Office of Michael A. Sanzo, LLC

(57) ABSTRACT

The present invention relates to a process for preparing mercaptoorganyl(alkoxysilanes), by hydrogenating bis(alkoxysilylorganyl) polysulphides with hydrogen in the presence of at least one alcohol and a doped metal catalyst. The doped metal catalyst comprises at least one substance from the group consisting of iron, iron compound, nickel, nickel compound, palladium, palladium compound, osmium, osmium compound, ruthenium, ruthenium compound, rhodium, rhodium compound, iridium and iridium compound plus at least one doping component.

20 Claims, No Drawings

U.S. PATENT DOCUMENTS

| | | |
|---|---|---|
| 2007/0049669 A1 | 3/2007 | Korth |
| 2007/0066760 A1 | 3/2007 | Korth |
| 2007/0203274 A1 | 8/2007 | Korth |

FOREIGN PATENT DOCUMENTS

| | | |
|---|---|---|
| DE | 2 035 619 | 7/1970 |
| DE | 33 14 742 A1 | 4/1983 |
| DE | 195 44 469 A1 | 3/1997 |
| DE | 196 51 849 A1 | 6/1998 |
| DE | 199 29 021 A1 | 6/1999 |
| DE | 100 40 678 C1 | 8/2000 |
| DE | 101 22 269 A1 | 11/2002 |
| DE | 103 51 735 B3 | 12/2004 |
| EP | 0 085 831 A2 | 8/1983 |
| EP | 0 086 271 A1 | 8/1983 |
| EP | 0 170 865 A1 | 2/1986 |
| EP | 0 323 699 A1 | 7/1989 |
| EP | 0 471 164 A1 | 2/1992 |
| EP | 0 652 245 A2 | 5/1995 |
| EP | 0 700 951 A1 | 3/1996 |
| EP | 0 848 006 A2 | 4/1998 |
| EP | 0 864 608 A1 | 9/1998 |
| EP | 0 949 263 A2 | 10/1999 |
| EP | 0 958 298 B1 | 11/1999 |
| EP | 0 978 525 A2 | 2/2000 |
| EP | 1 002 834 A1 | 5/2000 |
| EP | 1 130 023 A2 | 9/2001 |
| EP | 1 256 604 A2 | 11/2002 |
| EP | 1 285 926 A1 | 2/2003 |
| EP | 1 357 156 A2 | 10/2003 |
| EP | 1 394 167 A1 | 3/2004 |
| EP | 1 529 782 A1 | 5/2005 |
| EP | 1 538 152 A1 | 6/2005 |
| EP | 1 683 801 A2 | 7/2006 |
| EP | 1 700 861 A1 | 9/2006 |
| GB | 1 102 251 | 2/1968 |
| GB | 1 160 644 | 8/1969 |
| GB | 1 310 379 | 3/1973 |
| JP | 62-181346 | 8/1987 |
| JP | 8-291184 | 11/1996 |
| JP | 2004-99483 | 4/2004 |
| JP | 2005-47846 | 2/2005 |
| WO | WO 99/09036 | 2/1999 |
| WO | WO 02/31040 A2 | 4/2002 |
| WO | WO/2007/085521 A1 | 8/2007 |
| WO | WO/2007/141109 A1 | 12/2007 |

OTHER PUBLICATIONS

Sorokin, et al., "Synthesis of 1-(Organylthioalkyl)silatranes from 1-(Haloalkyl)silatranes," *J. Gen. Chem.* 69(3):394-398 (1999). Translated from *Zhurnal Obshchei Khimii* 69(3):407-412 (1999).

Sorokin, et al., "S-(Trimethoxysilymethyl)- and S-(Silatranylmethyl)isothiuronium Halides and Their N-Substituted Derivatives," *Russian J. Gen. Chem.* 74(4): 551-558 (2004). Translated from *Zhurnal Obshchei Khimii* 74(4): 603-610 (2004).

Voronkov, et al., 1-[(Acetylthio)alkyl]silatranes, *J. Gen. Chem. USSR* vol. 45(6): 1367 (Dec. 1975). Translated from *Zhurnal Obschei Khimii* 45(6): 1395 (Jun. 1975).

Voronkov, et al., "1-[(Organothio)alkyl]siltranes," *Russian J. Gen. Chem.* 49(3):529-536 (Sep. 1979). Translated from *Zhurnal Obshchei Khimii* 49(3):605-614 (Mar. 1979).

Voronkov, et al., "Photochemical Organothioation of 1-vinysilatrane and its c-methyl Derivatives," *Russian J. Gen. Chem.* 49(6):1130-1136 (Nov. 1979). Translated from *Zhurnal Obshchei Khimii* 49(6):1285-1292 (Jun. 1979).

Voronkov, et al., "O,O-Dialkyl-S-(1-Silatranylalkyl) Dithiophosphates," *Bull. Acad. Sci. USSR Div. Chem. Sci.* 36(8):1745-1747 (1988). Translated from *Izvestiya Akademii Nauk SSSR* 8:1882-1884 (Aug. 1987).

English language abstract for DE 33 14 742 A1, cited as reference B1 above.

English language abstract for DE 195 44 469 A1, cited as reference B2 above.

English language abstract for DE 196 51 849 A1, cited as reference B3 above.

English language abstract for DE 199 29 021 A1, cited as reference B4 above.

English language abstract for DE 100 40 678 C1, cited as reference B5 above.

English language abstract for DE 101 22 269 A1, cited as reference B6 above.

English language abstract for DE 103 51 735 B3, cited as reference B7 above.

English language abstract for EP 0 848 006 A2, cited as reference B15 above.

English language abstract for EP 0 978 525 A2, cited as reference B18 above.

English language abstract for EP 1 130 023 A2, cited as reference B20 above.

English language abstract for EP 1 256 604 A2, cited as reference B21 above.

English language abstract for EP 1 357 156 A2, cited as reference B23 above.

English language abstract for JP 62-181346, cited as reference B30 above.

English language abstract for JP 8-291184, cited as reference B31 above.

English language abstract for JP 2004-099483, cited as reference B32 above.

English language abstract for JP 2005-047846, cited as reference B33 above.

English language abstract for EP 1 394 167, cited as document B2 above.

English translation for WO/2007/141109, cited as document B5 above.

PROCESS FOR PREPARING MERCAPTOORGANYL (ALKOXYSILANES)

CROSS REFERENCE TO RELATED APPLICATIONS

The present application claims priority to German application DE 10 20052 020 535.6, filed on May 3, 2005, the contents of which is hereby incorporated by reference in its entirety.

FIELD OF THE INVENTION

The present invention relates to a process for preparing mercaptoorganyl(alkoxysilanes).

BACKGROUND OF THE INVENTION

U.S. Pat. No. 6,433,206 discloses a process for preparing silicon-containing organomercaptans by hydrogenating bis(organyl-silyl) polysulphides using group VIII metal catalysts which must be preserved from poisoning by water, $H_2S$ or alcohols. That process has the drawback that the conversion ("g of product silane" per "minute" per "mmol of catalyzing metal") under energy-sparing conditions is relatively low. The known reaction proceeds with satisfactory conversion only under high pressure and temperature conditions (>100 bar and >180° C.) which are difficult to realise technically, owing to the high load on the material for the plant.

DE 102004043094.2 discloses a process for preparing mercaptoorganyl(alkoxysilanes) that involves hydrogenating bis(alkoxysilylorganyl) polysulphides at temperatures of <190° C. and pressures of <100 bar with hydrogen and a transition metal catalyst and without adding water, alcohol or $H_2S$.

DE 102004043093.4, furthermore, discloses a process for preparing mercaptoorganyl(alkoxysilanes) that involves hydrogenating bis(alkoxysilylorganyl) polysulphides in a solvent with hydrogen and a transition metal catalyst without any alcohols, $H_2S$ or water.

DESCRIPTION OF THE INVENTION

It is an object of the present invention to provide a process for the reductive cleavage of bis(alkoxysilylorganyl) polysulphides that permits at least equal conversions under milder temperature and/or pressure conditions than the process known from U.S. Pat. No. 6,433,206.

The invention provides a process for preparing mercaptoorganyl(alkoxysilanes), by hydrogenating bis(alkoxy-silylorganyl) polysulphides with hydrogen in the presence of at least one alcohol and a doped metal catalyst, characterized in that the doped metal catalyst comprises at least one substance from the group consisting of iron, iron compound, nickel, nickel compound, palladium, palladium compound, osmium, osmium compound, ruthenium, ruthenium compound, rhodium, rhodium compound, iridium and iridium compound plus at least one doping component.

The bis(alkoxysilylorganyl) polysulphide may be in solution in the alcohol and may be a compound of the general formula (I):

$$Z\text{-}A\text{-}S_x\text{-}A\text{-}Z \quad (I)$$

in which x is a number from 1 to 14, preferably 1 to 8, more preferably 2 to 4, very preferably 2.0-2.6 and 3.2-3.9, Z is identical or different at each occurrence and is $SiX^1X^2X^3$ or $Si(OCH_2\text{—}CH_2\text{—})_3N$ where $X^1$, $X^2$ and $X^3$ each independently of one another can be a linear, branched or cyclic hydrocarbon chain having 1-18 carbon atoms (C1-C18), preferably having 1-10 carbon atoms (C1-C10), more preferably methyl, ethyl, propyl or butyl, a linear or branched alkyl acid group $(C_aH_{2a+1})$—C(=O)O— with a=1-25, such as acetoxy-$CH_3$—(C=O)O—, a linear or branched alkenyl acid substituent $(C_bH_{2b-1})$—C(=O)O— with b=2-25, a linear or branched, substituted alkyl or alkenyl acid group, an unsubstituted, halogen-substituted or alkyl-substituted cycloalkane radical having 5-12 carbon atoms, a benzyl radical, a halogen-substituted or alkyl-substituted phenyl radical, alkoxy groups with linear and/or branched hydrocarbon chains, preferably $(C_1\text{-}C_{24})$alkoxy, more preferably methoxy-($CH_3O$—), ethoxy-$C_2H_5O$—), propoxy-($C_3H_7O$), butoxy-($C_4H_9O$—), dodecyloxy-($C_{12}H_{25}O$—), tetradecyloxy-($C_{14}H_{29}O$—), hexadecyloxy-($C_{16}H_{33}O$—) or octadecyloxy-($C_{18}H_{37}O$—), a cycloalkoxy group having 5-12 carbon atoms, cyclohexanol for example, a halogen-substituted or alkyl-substituted phenoxy group or a benzyloxy group, an alkyl ether group O—$(CR^I{}_2\text{—}CR^I{}_2)$—O-Alk or alkyl polyether group O—$(CR^I{}_2\text{—}CR^I{}_2O)_y$—Alk, with y=2-25, preferably y=2-15, more preferably y=3-10, very preferably y=3-6, $R^I$ independently at each occurrence is H or an alkyl group, preferably a $CH_3$ group, Alk is a linear or branched, saturated or unsaturated alkyl chain having 1-30 carbon atoms (C1-C30), preferably C1-C20, more preferably C4-C18, very preferably C8-C16, and A is a linear or branched, saturated or unsaturated aliphatic, aromatic or mixedly aliphatic/aromatic divalent $C_1\text{-}C_{30}$ hydrocarbon chain, preferably $C_1\text{-}C_4$, more preferably (—$CH_2$—), (—$CH_2$—)$_2$, (—$CH_2$—)$_3$, (—CH($CH_3$)—$CH_2$—), (—$CH_2$—CH($CH_3$)—), (—$CH_2$—$CH_2$—CH($CH_3$)—) or (—$CH_2$—CH($CH_3$)—$CH_2$—).

The alkyl polyether group may include ethylene oxide ($CH_2$—$CH_2$—O) and propylene oxide (CH($CH_3$)—$CH_2$—O) or ($CH_2$—CH($CH_3$)—O) units, distributed randomly or in blocks. The alkyl polyether group O—$(CR^I{}_2\text{—}CR^I{}_2O)_y$-Alk may be O—($CH_2$—$CH_2O)_2$—$C_8H_{17}$, O—($CH_2$—$CH_2O)_3$—$C_8H_{17}$, O—($CH_2$—$CH_2O)_4$—$C_8H_{17}$, O—($CH_2$—$CH_2O)_5$—$C_8H_{17}$, O—($CH_2$—$CH_2O)_6$—$C_8H_{17}$, O—($CH_2$—$CH_2O)_7$—$C_8H_{17}$, O—(CH($CH_3$)—$CH_2O)_2$—$C_8H_{17}$, O—(CH($CH_3$)—$CH_2O)_3$—$C_8H_{17}$, O—(CH($CH_3$)—$CH_2O)_4$—$C_8H_{17}$, O—(CH($CH_3$)—$CH_2O)_5$—$C_8H_{17}$, O—(CH($CH_3$)—$CH_2O)_6$—$C_8H_{17}$, O—(CH($CH_3$)—$CH_2O)_7$—$C_8H_{17}$, O—($CH_2$—$CH_2O)_2$—$C_9H_{19}$, O—($CH_2$—$CH_2O)_3$—$C_9H_{19}$, O—($CH_2$—$CH_2O)_4$—$C_9H_{19}$, O—($CH_2$—$CH_2O)_5$—$C_9H_{19}$, O—($CH_2$—$CH_2O)_6$—$C_9H_{19}$, O—($CH_2$—$CH_2O)_7$—$C_9H_{19}$, O—(CH($CH_3$)—$CH_2O)_2$—$C_9H_{19}$, O—(CH($CH_3$)—$CH_2O)_3$—$C_9H_{19}$, O—(CH($CH_3$)—$CH_2O)_4$—$C_9H_{19}$, O—(CH($CH_3$)—$CH_2O)_5$—$C_9H_{19}$, O—(CH($CH_3$)—$CH_2O)_6$—$C_9H_{19}$, O—(CH($CH_3$)—$CH_2O)_7$—$C_9H_{19}$, O—($CH_2$—$CH_2O)_2$—$C_{10}H_{21}$, O—($CH_2$—$CH_2O)_3$—$C_{10}H_{21}$, O—($CH_2$—$CH_2O)_4$—$C_{10}H_{21}$, O—($CH_2$—$CH_2O)_5$—$C_{10}H_{21}$, O—($CH_2$—$CH_2O)_6$—$C_{10}H_{21}$, O—($CH_2$—$CH_2O)_7$—$C_{10}H_{21}$, O—(CH($CH_3$)—$CH_2O)_2$—$C_{10}H_{21}$, O—(CH($CH_3$)—$CH_2O)_3$—$C_{10}H_{21}$, O—(CH($CH_3$)—$CH_2O)_4$—$C_{10}H_{21}$, O—(CH($CH_3$)—$CH_2O)_5$—$C_{10}H_{21}$, O—(CH($CH_3$)—$CH_2O)_6$—$C_{10}H_{21}$, O—(CH($CH_3$)—$CH_2O)_7$—$C_{10}H_{21}$, O—($CH_2$—$CH_2O)_2$—$C_{11}H_{23}$, O—($CH_2$—$CH_2O)_3$—$C_{11}H_{23}$, O—($CH_2$—$CH_2O)_4$—$C_{11}H_{23}$, O—($CH_2$—$CH_2O)_5$—$C_{11}H_{23}$, O—($CH_2$—$CH_2O)_6$—$C_{11}H_{23}$, O—($CH_2$—$CH_2O)_7$—$C_{11}H_{23}$, O—(CH($CH_3$)—$CH_2O)_2$—$C_{11}H_{23}$, O—(CH($CH_3$)—$CH_2O)_3$—$C_{11}H_{23}$, O—(CH($CH_3$)—$CH_2O)_4$—$C_{11}H_{23}$, O—(CH($CH_3$)—$CH_2O)_5$—$C_{11}H_{23}$, O—(CH($CH_3$)—$CH_2O)_6$—$C_{11}H_{23}$, O—(CH($CH_3$)—$CH_2O)_7$—

$C_{11}H_{23}$, O—$(CH_2$—$CH_2O)_2$—$C_{12}H_{25}$, O—$(CH_2$—$CH_2O)_3$—$C_{12}H_{25}$, O—$(CH_2$—$CH_2O)_4$—$C_{12}H_{25}$, O—$(CH_2$—$CH_2O)_5$—$C_{12}H_{25}$, O—$(CH_2$—$CH_2O)_6$—$C_{12}H_{25}$, O—$(CH_2$—$CH_2O)_7$—$C_{12}H_{25}$, O—$(CH(CH_3)$—$CH_2O)_2$—$C_{12}H_{25}$, O—$(CH(CH_3)$—$CH_2O)_3$—$C_{12}H_{25}$, O—$(CH(CH_3)$—$CH_2O)_4$—$C_{12}H_{25}$, O—$(CH(CH_3)$—$CH_2O)_5$—$C_{12}H_{25}$, O—$(CH(CH_3)$—$CH_2O)_6$—$C_{12}H_{25}$, O—$(CH(CH_3)$—$CH_2O)_7$—$C_{12}H_{25}$, O—$(CH_2$—$CH_2O)_2$—$C_{13}H_{27}$, O—$(CH_2$—$CH_2O)_3$—$C_{13}H_{27}$, O—$(CH_2$—$CH_2O)_4$—$C_{13}H_{27}$, O—$(CH_2$—$CH_2O)_5$—$C_{13}H_{27}$, O—$(CH_2$—$CH_2O)_6$—$C_{13}H_{27}$, O—$(CH_2$—$CH_2O)_7$—$C_{13}H_{27}$, O—$(CH(CH_3)$—$CH_2O)_2$—$C_{13}H_{27}$, O—$(CH(CH_3)$—$CH_2O)_3$—$C_{13}H_{27}$, O—$(CH(CH_3)$—$CH_2O)_4$—$C_{13}H_{27}$, O—$(CH(CH_3)$—$CH_2O)_5$—$C_{13}H_{27}$, O—$(CH(CH_3)$—$CH_2O)_6$—$C_{13}H_{27}$, O—$(CH(CH_3)$—$CH_2O)_7$—$C_{13}H_{27}$, O—$(CH_2$—$CH_2O)_2$—$C_{14}H_{29}$, O—$(CH_2$—$CH_2O)_3$—$C_{14}H_{29}$, O—$(CH_2$—$CH_2O)_4$—$C_{14}H_{29}$, O—$(CH_2$—$CH_2O)_5$—$C_{14}H_{29}$, O—$(CH_2$—$CH_2O)_6$—$C_{14}H_{29}$, O—$(CH_2$—$CH_2O)_7$—$C_{14}H_{29}$, O—$(CH(CH_3)$—$CH_2O)_2$—$C_{14}H_{29}$, O—$(CH(CH_3)$—$CH_2O)_3$—$C_{14}H_{29}$, O—$(CH(CH_3)$—$CH_2O)_4$—$C_{14}H_{29}$, O—$(CH(CH_3)$—$CH_2O)_5$—$C_{14}H_{29}$, O—$(CH(CH_3)$—$CH_2O)_6$—$C_{14}H_{29}$, O—$(CH(CH_3)$—$CH_2O)_7$—$C_{14}H_{29}$, O—$(CH_2$—$CH_2O)_2$—$C_{15}H_{31}$, O—$(CH_2$—$CH_2O)_3$—$C_{15}H_{31}$, O—$(CH_2$—$CH_2O)_4$—$C_{15}H_{31}$, O—$(CH_2$—$CH_2O)_5$—$C_{15}H_{31}$, O—$(CH_2$—$CH_2O)_6$—$C_{15}H_{31}$, O—$(CH_2$—$CH_2O)_7$—$C_{15}H_{31}$, O—$(CH(CH_3)$—$CH_2O)_2$—$C_{15}H_{31}$, O—$(CH(CH_3)$—$CH_2O)_3$—$C_{15}H_{31}$, O—$(CH(CH_3)$—$CH_2O)_4$—$C_{15}H_{31}$, O—$(CH(CH_3)$—$CH_2O)_5$—$C_{15}H_{31}$, O—$(CH(CH_3)$—$CH_2O)_6$—$C_{15}H_{31}$, O—$(CH(CH_3)$—$CH_2O)_7$—$C_{15}H_{31}$, O—$(CH_2$—$CH_2O)_2$—$C_{16}H_{33}$, O—$(CH_2$—$CH_2O)_3$—$C_{16}H_{33}$, O—$(CH_2$—$CH_2O)_4$—$C_{16}H_{33}$, O—$(CH_2$—$CH_2O)_5$—$C_{16}H_{33}$, O—$(CH_2$—$CH_2O)_6$—$C_{16}H_{33}$, O—$(CH_2$—$CH_2O)_7$—$C_{16}H_{33}$, O—$(CH(CH_3)$—$CH_2O)_2$—$C_{16}H_{33}$, O—$(CH(CH_3)$—$CH_2O)_3$—$C_{16}H_{33}$, O—$(CH(CH_3)$—$CH_2O)_4$—$C_{16}H_{33}$, O—$(CH(CH_3)$—$CH_2O)_5$—$C_{16}H_{33}$, O—$(CH(CH_3)$—$CH_2O)_6$—$C_{16}H_{33}$ or O—$(CH(CH_3)$—$CH_2O)_7$—$C_{16}H_{33}$.

A may be linear or branched and may contain saturated and unsaturated bonds. A may be substituted by, instead of H, any of a very wide variety of substituents, independently of one another, such as, for example, —CN, —SH, —$NH_2$, halogens, for example —Cl, —Br or —F, alcohol functionalities —OH or Alkoxides —O-alkyl. As A it is possible to use $CH_2$, $CH_2CH_2$, $CH_2CH_2CH_2$, $CH_2CH(CH_3)$, $CH_2CH_2CH_2CH_2$, $CH_2CH_2CH(CH_3)$, $CH_2CH(CH_3)CH_2$, $CH_2CH_2CH_2CH_2CH_2$, $CH_2CH(CH_3)CH_2CH_2$, $CH_2CH_2CH(CH_3)CH_2$, $CH(CH_3)CH_2CH(CH_3)$ or $CH_2CH(CH_3)CH(CH_3)$.

As the silane of the general formula (I) it is possible to use, for example, the following compounds:

$[(MeO)_3Si(CH_2)_3]_2S_2$, $[(MeO)_3Si(CH_2)_3]_2S_3$, $[(MeO)_3Si(CH_2)_3]_2S_4$, $[(MeO)_3Si(CH_2)_3]_2S_5$, $[(MeO)_3Si(CH_2)_3]_2S_6$, $[(MeO)_3Si(CH_2)_3]_2S_7$, $[(MeO)_3Si(CH_2)_3]_2S_8$, $[(MeO)_3Si(CH_2)_3]_2S_9$, $[(MeO)_3Si(CH_2)_3]_2S_{10}$, $[(MeO)_3Si(CH_2)_3]_2S_{11}$, $[(MeO)_3Si(CH_2)_3]_2S_{12}$, $[(EtO)_3Si(CH_2)_3]_2S_2$, $[(EtO)_3Si(CH_2)_3]_2S_3$, $[(EtO)_3Si(CH_2)_3]_2S_4$, $[(EtO)_3Si(CH_2)_3]_2S_5$, $[(EtO)_3Si(CH_2)_3]_2S_6$, $[(EtO)_3Si(CH_2)_3]_2S_7$, $[(EtO)_3Si(CH_2)_3]_2S_8$, $[(EtO)_3Si(CH_2)_3]_2S_9$, $[(EtO)_3Si(CH_2)_3]_2S_{10}$, $[(EtO)_3Si(CH_2)_3]_2S_{11}$, $[(EtO)_3Si(CH_2)_3]_2S_{12}$, $[(EtO)_3Si(CH_2)_3]_2S_{13}$, $[(EtO)_3Si(CH_2)_3]_2S_{14}$, $[(C_3H_7O)_3Si(CH_2)_3]_2S_2$, $[(C_3H_7O)_3Si(CH_2)_3]_2S_3$, $[(C_3H_7O)_3Si(CH_2)_3]_2S_4$, $[(C_3H_7O)_3Si(CH_2)_3]_2S_5$, $[(C_3H_7O)_3Si(CH_2)_3]_2S_6$, $[(C_3H_7O)_3Si(CH_2)_3]_2S_7$, $[(C_3H_7O)_3Si(CH_2)_3]_2S_8$, $[(C_3H_7O)_3Si(CH_2)_3]_2S_9$, $[(C_3H_7O)_3Si(CH_2)_3]_2S_{10}$, $[(C_3H_7O)_3Si(CH_2)_3]_2S_{11}$, $[(C_3H_7O)_3Si(CH_2)_3]_2S_{12}$, $[(C_3H_7O)_3Si(CH_2)_3]_2S_{13}$, $[(C_3H_7O)_3Si(CH_2)_3]_2S_{14}$, $[(C_{12}H_{25}O)(EtO)_2Si(CH_2)_3]S_x[(CH_2)_3Si(OEt)_3]$, $[(C_{12}H_{25}O)_2(EtO)Si(CH_2)_3]S_x[(CH_2)_3Si(OEt)_3]$, $[(C_{12}H_{25}O)_3Si(CH_2)_3]S_x[(CH_2)_3Si(OEt)_3]$, $[(C_{12}H_{25}O)(EtO)_2Si(CH_2)_3]S_x[(CH_2)_3Si(C_{12}H_{25}O)(OEt)_2]$, $[(C_{12}H_{25}O)_2(EtO)Si(CH_2)_3]S_x[(CH_2)_3Si(C_{12}H_{25}O)(OEt)_2]$, $[(C_{12}H_{25}O)_3Si(CH_2)_3]S_x[(CH_2)_3Si(C_{12}H_{25}O)(OEt)_2]$, $[(C_{12}H_{25}O)(EtO)_2Si(CH_2)_3]S_x[(CH_2)_3Si(C_{12}H_{25}O)_2(OEt)]$, $[(C_{12}H_{25}O)_2(EtO)Si(CH_2)_3]S_x[(CH_2)_3Si(C_{12}H_{25}O)_2(OEt)]$, $[(C_{12}H_{25}O)_3Si(CH_2)_3]S_x[(CH_2)_3Si(C_{12}H_{25}O)_2(OEt)]$, $[(C_{12}H_{25}O)(EtO)_2Si(CH_2)_3]S_x[(CH_2)_3Si(C_{12}H_{25}O)_3]$, $[(C_{12}H_{25}O)_2(EtO)Si(CH_2)_3]S_x[(CH_2)_3Si(C_{12}H_{25}O)_3]$, $[(C_{12}H_{25}O)_3Si(CH_2)_3]S_x[(CH_2)_3Si(C_{12}H_{25}O)_3]$, $[(C_{14}H_{29}O)(EtO)_2Si(CH_2)_3]S_x[(CH_2)_3Si(OEt)_3]$, $[(C_{14}H_{29}O)_2(EtO)Si(CH_2)_3]S_x[(CH_2)_3Si(OEt)_3]$, $[(C_{14}H_{29}O)_3Si(CH_2)_3]S_x[(CH_2)_3Si(OEt)_3]$, $[(C_{14}H_{29}O)(EtO)_2Si(CH_2)_3]S_x[(CH_2)_3Si(C_{14}H_{29}O)(OEt)_2]$, $[(C_{14}H_{29}O)_2(EtO)Si(CH_2)_3]S_x[(CH_2)_3Si(C_{14}H_{29}O)(OEt)_2]$, $[(C_{14}H_{29}O)_3Si(CH_2)_3]S_x[(CH_2)_3Si(C_{14}H_{29}O)(OEt)_2]$, $[(C_{14}H_{29}O)(EtO)_2Si(CH_2)_3]S_x[(CH_2)_3Si(C_{14}H_{29}O)_2(OEt)]$, $[(C_{14}H_{29}O)_2(EtO)Si(CH_2)_3]S_x[(CH_2)_3Si(C_{14}H_{29}O)_2(OEt)]$, $[(C_{14}H_{29}O)_3Si(CH_2)_3]S_x[(CH_2)_3Si(C_{14}H_{29}O)_2(OEt)]$, $[(C_{14}H_{29}O)(EtO)_2Si(CH_2)_3]S_x[(CH_2)_3Si(C_{14}H_{29}O)_3]$, $[(C_{14}H_{29}O)_2(EtO)Si(CH_2)_3]S_x[(CH_2)_3Si(C_{14}H_{29}O)_3]$, $[(C_{14}H_{29}O)_3Si(CH_2)_3]S_x[(CH_2)_3Si(C_{14}H_{29}O)_3]$, $[(C_{16}H_{33}O)(EtO)_2Si(CH_2)_3]S_x[(CH_2)_3Si(OEt)_3]$, $[(C_{16}H_{33}O)_2(EtO)Si(CH_2)_3]S_x[(CH_2)_3Si(OEt)_3]$, $[(C_{16}H_{33}O)_3Si(CH_2)_3]S_x[(CH_2)_3Si(OEt)_3]$, $[(C_{16}H_{33}O)(EtO)_2Si(CH_2)_3]S_x[(CH_2)_3Si(C_{16}H_{33}O)(OEt)_2]$, $[(C_{16}H_{33}O)_2(EtO)Si(CH_2)_3]S_x[(CH_2)_3Si(C_{16}H_{33}O)(OEt)_2]$, $[(C_{16}H_{33}O)_3Si(CH_2)_3]S_x[(CH_2)_3Si(C_{16}H_{33}O)(OEt)_2]$, $[(C_{16}H_{33}O)(EtO)_2Si(CH_2)_3]S_x[(CH_2)_3Si(C_{16}H_{33}O)_2(OEt)]$, $[(C_{16}H_{33}O)_2(EtO)Si(CH_2)_3]S_x[(CH_2)_3Si(C_{16}H_{33}O)_2(OEt)]$, $[(C_{16}H_{33}O)_3Si(CH_2)_3]S_x[(CH_2)_3Si(C_{16}H_{33}O)_2(OEt)]$, $[(C_{16}H_{33}O)(EtO)_2Si(CH_2)_3]S_x[(CH_2)_3Si(C_{16}H_{33}O)_3]$, $[(C_{16}H_{33}O)_2(EtO)Si(CH_2)_3]S_x[(CH_2)_3Si(C_{16}H_{33}O)_3]$, $[(C_{16}H_{33}O)_3Si(CH_2)_3]S_x[(CH_2)_3Si(C_{16}H_{33}O)_3]$, $[(C_{18}H_{37}O)(EtO)_2Si(CH_2)_3]S_x[(CH_2)_3Si(OEt)_3]$, $[(C_{18}H_{37}O)_2(EtO)Si(CH_2)_3]S_x[(CH_2)_3Si(OEt)_3]$, $[(C_{18}H_{37}O)_3Si(CH_2)_3]S_x[(CH_2)_3Si(OEt)_3]$, $[(C_{18}H_{37}O)(EtO)_2Si(CH_2)_3]S_x[(CH_2)_3Si(C_{18}H_{37}O)(OEt)_2]$, $[(C_{18}H_{37}O)_2(EtO)Si(CH_2)_3]S_x[(CH_2)_3Si(C_{18}H_{37}O)(OEt)_2]$, $[(C_{18}H_{37}O)_3Si(CH_2)_3]S_x[(CH_2)_3Si(C_{18}H_{37}O)(OEt)_2]$, $[(C_{18}H_{37}O)(EtO)_2Si(CH_2)_3]S[(CH_2)_3Si(C_{18}H_{37}O)_2(OEt)]$, $[(C_{18}H_{37}O)_2(EtO)Si(CH_2)_3]S_x[(CH_2)_3Si(C_{18}H_{37}O)_2(OEt)]$, $[(C_{18}H_{37}O)_3Si(CH_2)_3]S_x[(CH_2)_3Si(C_{18}H_{37}O)_2(OEt)]$, $[(C_{18}H_{37}O)(EtO)_2Si(CH_2)_3]S_x[(CH_2)_3Si(C_{18}H_{37}O)_3]$, $[(C_{18}H_{37}O)_2(EtO)Si(CH_2)_3]S_x[(CH_2)_3Si(C_{18}H_{37}O)_3]$, $[(C_{18}H_{37}O)_3Si(CH_2)_3]S_x[(CH_2)_3Si(C_{18}H_{37}O)_3]$

The bis(alkoxysilylorganyl) polysulphide starting materials used may be a mixture of different bis(alkoxysilylorganyl) polysulphides with —$S_1$— to —$S_{14}$— (x=1-14) or a single bis(alkoxysilylorganyl) polysulphide with x=2-14.

Bis(alkoxysilylorganyl) polysulphides used may be compounds or mixtures of compounds having an average sulphur chain length of 2.0 to 4.0. The average sulphur chain length for bis(alkoxysilylorganyl) polysulphides may be determined as an arithmetic mean of $S_2$ to $S_{14}$, measured by HPLC. Preferably compounds have an average chain length of $S_x=S_{2.0}$ to $S_{2.6}$ and $S_x=S_{3.2}$ to $S_{3.9}$. Particularly preferred are bis(alkoxysilylorganyl) disulphides having an average chain length of 2.0 to 2.6, since in comparison to bis(alkoxysilylorganyl) polysulphides with $S_x=S_{2.7}$ to $S_{3.9}$ it is possible to achieve higher conversions in g product/min/mmol catalyst and for less $H_2S$ to be released.

The group Z=—SiX$^1$X$^2$X$^3$ in formula I can with preference be —Si(OMe)$_3$, —Si(OEt)$_3$, —SiMe(OMe)$_2$, —SiMe(OEt)$_2$), —SiMe$_2$(OMe) —SiMe$_2$(OEt), —Si[—O(CO)CH$_3$]$_3$, —Si(OC$_{12}$H$_{25}$)$_3$, Si(OC$_{14}$H$_{29}$)$_3$, Si(OC$_{16}$H$_{33}$)$_3$, Si(OC$_{18}$H$_{37}$)$_3$, Si(OC$_{14}$H$_{29}$)$_2$(OC$_{16}$H$_{33}$), Si(OC$_{14}$H$_{29}$)$_2$ (OC$_{18}$H$_{37}$), Si(OC$_{16}$H$_{33}$)$_2$(OC$_{14}$H$_{29}$), Si(OC$_{16}$H$_{33}$)$_2$ (OC$_{18}$H$_{37}$), Si(OC$_{18}$H$_{37}$)$_2$(OC$_{16}$H$_{33}$) or Si(OC$_{14}$H$_{29}$) (OC$_{18}$H$_{37}$)$_2$.

The mercaptoorganyl(alkoxysilane) product may be a compound of the general formula (II)

W-A-SH  (II)

wherein W=—SiY$^1$Y$^2$Y$^3$ or Si(OCH$_2$—CH$_2$—)$_3$N, with Y$^1$, Y$^2$ and Y$^3$ independently of one another able to be X$^1$, X$^2$, X$^3$ or hydroxyl (—OH) and with X$^1$, X$^2$, X$^3$ and A, in each case independently of one another, having the definition as per formula (I).

The group W=—SiY$^1$Y$^2$Y$^3$ in formula II may with preference be —Si(OMe)$_3$, —Si(OMe)$_2$OH, —Si(OMe) (OH)$_2$, —Si(OEt)$_3$, —Si(OEt)$_2$OH, —Si(OEt) (OH)$_2$, —SiMe (OMe)$_2$, —SiMe(OEt)$_2$), —SiMe(OH)$_2$, —SiMe$_2$(OMe), —SiMe$_2$(OEt), SiMe$_2$(OH), —Si[—O(CO)CH$_3$]$_3$, —Si (OC$_{12}$H$_{25}$)$_3$, Si(OC$_{14}$H$_{29}$)$_3$, Si(OC$_{16}$H$_{33}$)$_3$, Si(OC$_{18}$H$_{37}$)$_3$, Si(OC$_{14}$H$_{29}$)$_2$ (OC$_{16}$H$_{33}$), Si(OC$_{14}$H$_{29}$)$_2$ (OC$_{18}$H$_{37}$), Si(OC$_{16}$H$_{33}$)$_2$ (OC$_{14}$H$_{29}$), Si(OC$_{16}$H$_{33}$)$_2$ (OC$_{18}$H$_{37}$), Si(OC$_{18}$H$_{37}$)$_2$ (OC$_{16}$H$_{33}$) or Si(OC$_{14}$H$_{29}$) (OC$_{18}$H$_{37}$)$_2$.

Mercaptoorganyl(alkoxysilanes) of the general formula (II) may for example be the following:

3-mercaptopropyl(trimethoxysilane), 3-mercaptopropyl(dimethoxyhydroxysilane), 3-mercaptopropyl(triethoxysilane), 3-mercaptopropyl(diethoxyhydroxysilane), 3-mercaptopropyl(diethoxymethoxysilane), 3-mercaptopropyl(tripropoxysilane), 3-mercaptopropyl(dipropoxymethoxysilane), 3-mercaptopropyl(dipropoxyhydroxysilane), 3-mercaptopropyl(tridodecanoxysilane), 3-mercaptopropyl(didodecanoxyhydroxysilane), 3-mercaptopropyl(tritetradecanoxysilane), 3-mercaptopropyl(trihexadecanoxysilane), 3-mercaptopropyl(trioctadecanoxysilane), 3-mercaptopropyl(didodecanoxy) tetradecanoxysilane, 3-mercaptopropyl(dodecanoxy) tetradecanoxy(hexadecanoxy) silane, 3-mercaptopropyl (dimethoxymethylsilane), 3-mercaptopropyl (methoxymethylhydroxysilane), 3-mercaptopropyl (methoxydimethylsilane), 3-mercaptopropyl (hydroxydimethylsilane), 3-mercaptopropyl (diethoxymethylsilane), 3-mercaptopropyl (ethoxyhydroxymethylsilane), 3-mercaptopropyl (ethoxydimethylsilane), 3-mercaptopropyl (dipropoxymethylsilane), 3-mercaptopropyl (propoxymethylhydroxysilane), 3-mercaptopropyl (propoxydimethylsilane), 3-mercaptopropyl (diisopropoxymethylsilane), 3-mercaptopropyl (isopropoxydimethylsilane), 3-mercaptopropyl (dibutoxymethylsilane), 3-mercaptopropyl (butoxydimethylsilane), 3-mercaptopropyl (disiobutoxymethylsilane), 3-mercaptopropyl (siobutoxymethylhydroxysilane), 3-mercaptopropyl (isobutoxydimethylsilane), 3-mercaptopropyl (didodecanoxymethylsilane), 3-mercaptopropyl (dodecanoxydimethylsilane), 3-mercaptopropyl (ditetradecanoxymethylsilane), 3-mercaptopropyl (tetradecanoxymethylhydroxysilane), 3-mercaptopropyl (tetradecanoxydimethylsilane), 2-mercaptoethyl (trimethoxysilane), 2-mercaptoethyl(triethoxysilane), 2-mercaptoethyl(diethoxymethoxysilane), 2-mercaptoethyl(tripropoxysilane), 2-mercaptoethyl(dipropoxymethoxysilane), 2-mercaptoethyl(tridodecanoxysilane), 2-mercaptoethyl(tritetradecanoxysilane), 2-mercaptoethyl(trihexadecanoxysilane), 2-mercaptoethyl(trioctadecanoxysilane), 2-mercaptoethyl(didodecanoxy)tetradecanoxysilan, 2-mercaptoethyl(dodecanoxy) tetradecanoxy(hexadecanoxy) silane, 2-mercaptoethyl (dimethoxymethylsilane), 2-mercaptoethyl (methoxymethylhydroxysilane), 2-mercaptoethyl (methoxydimethylsilane), 2-mercaptoethyl (diethoxymethylsilane), 2-mercaptoethyl (ethoxydimethylsilane), 2-mercaptoethyl (hydroxydimethylsilane), 1-mercaptomethyl (trimethoxysilane), 1-mercaptomethyl(triethoxysilane), 1-mercaptomethyl(diethoxymethoxysilane), 1-mercaptomethyl(diethoxyhydroxysilane), 1-mercaptomethyl(dipropoxymethoxyslane), 1-mercaptomethyl(tripropoxysilane), 1-mercaptomethyl(trimethoxysilane), 1-mercaptomethyl(dimethoxymethylsilane), 1-mercaptomethyl(methoxydimethylsilane), 1-mercaptomethyl(diethoxymethylsilane), 1-mercaptomethyl(ethoxymethylihydroxysilane), 1-mercaptomethyl (ethoxydimethylsilane), 3-mercaptobutyl (trimethoxysilane), 3-mercaptobutyl(triethoxysilane), 3-mercaptobutyl(diethoxymethoxysilane) 3-mercaptobutyl(tripropoxysilane), 3-mercaptobutyl(dipropoxymethoxysilane), 3-mercaptobutyl(dimethoxymethylsilane), 3-mercaptobutyl(diethoxymethylsilane), 3-mercaptobutyl(dimethylmethoxysilane), 3-mercaptobutyl(dimethylethoxysilane), 3-mercaptobutyl(dimethyhydroxysilane), 3-mercaptobutyl(tridodecanoxysilane), 3-mercaptobutyl(tritetradecanoxysilane), 3-mercaptobutyl(trihexadecanoxysilane), 3-mercaptobutyl(didodecanoxy)tetradecanoxysilan, 3-mercaptobutyl(dodecanoxy) tetradecanoxy(hexadecanoxy) silane, 3-mercapto-2-methyl-propyl(trimethoxysilane), 3-mercapto-2-methyl-propyl(triethoxysilane), 3-mercapto-2-methyl-propyl (diethoxymethoxysilane), 3-mercapto-2-methyl-propyl (tripropoxysilane), 3-mercapto-2-methyl-propyl (dipropoxymethoxysilane), 3-mercapto-2-methyl-propyl (tridodecanoxysilane), 3-mercapto-2-methyl-propyl (tritetradecanoxysilane), 3-mercapto-2-methyl-propyl (trihexadecanoxysilane), 3-mercapto-2-methyl-propyl (trioctadecanoxysilane), 3-mercapto-2-methyl-propyl (didodecanoxy)tetradecanoxysilane, 3-mercapto-2-methyl-propyl(dodecanoxy)tetradecanoxy-(hexadecanoxy)silane, 3-mercapto-2-methyl-propyl (dimethoxymethylsilane), 3-mercapto-2-methyl-propyl (methoxydimethylsilane), 3-mercapto-2-methyl-propyl (diethoxymethylsilane), 3-mercapto-2-methyl-propyl (ethoxydimethylsilane), 3-mercapto-2-methyl-propyl (hydroxydimethylsilane), 3-mercapto-2-methyl-propyl (dipropoxymethylsilane), 3-mercapto-2-methyl-propyl (propoxydimethylsilane), 3-mercapto-2-methyl-propyl (diisopropoxymethylsilane), 3-mercapto-2-methyl-propyl (isopropoxydimethylsilane), 3-mercapto-2-methyl-propyl (dibutoxymethylsilane), 3-mercapto-2-methyl-propyl (butoxydimethylsilane), 3-mercapto-2-methyl-propyl (diisobutoxymethylsilane), 3-mercapto-2-methyl-propyl (isobutoxydimethylsilane), 3-mercapto-2-methyl-propyl (didodecanoxymethylsilane), 3-mercapto-2-methyl-propyl(dodecanoxydimethylsilane), 3-mercapto-2-methyl-propyl(ditetradecanoxymethylsilane), 3-mercapto-2-methyl-propyl(tetradecanoxydimethylsilane), [(C$_9$H$_{19}$O—(CH$_2$—CH$_2$O)$_2$](MeO)$_2$Si(CH$_2$)$_3$SH, [(C$_9$H$_{19}$O—(CH$_2$—CH$_2$O)$_3$](MeO)$_2$Si(CH$_2$)$_3$SH, [(C$_9$H$_9$O—(CH$_2$—CH$_2$O)$_4$](MeO)$_2$Si(CH$_2$)$_3$SH, [(C$_9$H$_9$O—(CH$_2$—CH$_2$O)$_5$](MeO)$_2$Si(CH$_2$)$_3$SH,

[(C_9H_{19}O—(CH_2—CH_2O)_6](MeO)_2Si(CH_2)_3SH,
[(C_{12}H_{25}O—(CH_2—CH_2O)_2](MeO)_2Si(CH_2)_3SH,
[(C_{12}H_{25}O—(CH_2—CH_2O)_3](MeO)_2Si(CH_2)_3SH,
[(C_{12}H_{25}O—(CH_2—CH_2O)_4](MeO)_2Si(CH_2)_3SH,
[(C_{12}H_{25}O—(CH_2—CH_2O)_5](MeO)_2Si(CH_2)_3SH,
[(C_{12}H_{25}O—(CH_2—CH_2O)_6](MeO)_2Si(CH_2)_3SH,
[(C_{13}H_{27}O—(CH_2—CH_2O)_2](MeO)_2Si(CH_2)_3SH,
[(C_{13}H_{27}O—(CH_2—CH_2O)_3](MeO)_2Si(CH_2)_3SH,
[(C_{13}H_{27}O—(CH_2—CH_2O)_4](MeO)_2Si(CH_2)_3SH,
[(C_{13}H_{27}O—(CH_2—CH_2O)_5](MeO)_2Si(CH_2)_3SH,
[(C_{13}H_{27}O—(CH_2—CH_2O)_6](MeO)_2Si(CH_2)_3SH,
[(C_{14}H_{29}O—(CH_2—CH_2O)_2](MeO)_2Si(CH_2)_3SH,
[(C_{14}H_{29}O—(CH_2—CH_2O)_3](MeO)_2Si(CH_2)_3SH,
[(C_{14}H_{29}O—(CH_2—CH_2O)_4](MeO)_2Si(CH_2)_3SH,
[(C_{14}H_{29}O—(CH_2—CH_2O)_5](MeO)_2Si(CH_2)_3SH,
[(C_{14}H_{29}O—(CH_2—CH_2O)_6](MeO)_2Si(CH_2)_3SH,
[(C_9H_{19}O—(CH_2—CH_2O)_2]_2(MeO)Si(CH_2)_3SH,
[(C_9H_{19}O—(CH_2—CH_2O)_3]_2(MeO)Si(CH_2)_3SH,
[(C_9H_{19}O—(CH_2—CH_2O)_4]_2(MeO)Si(CH_2)_3SH,
[(C_9H_{19}O—(CH_2—CH_2O)_5]_2(MeO)Si(CH_2)_3SH,
[(C_9H_{19}O—(CH_2—CH_2O)_6]_2(MeO)Si(CH_2)_3SH,
[(C_{12}H_{25}O—(CH_2—CH_2O)_2]_2(MeO)Si(CH_2)_3SH,
[(C_{12}H_{25}O—(CH_2—CH_2O)_3]_2(MeO)Si(CH_2)_3SH,
[(C_{12}H_{25}O—(CH_2—CH_2O)_4]_2(MeO)Si(CH_2)_3SH,
[(C_{12}H_{25}O—(CH_2—CH_2O)_5]_2(MeO)Si(CH_2)_3SH,
[(C_{12}H_{25}O—(CH_2—CH_2O)_6]_2(MeO)Si(CH_2)_3SH,
[(C_{13}H_{27}O—(CH_2—CH_2O)_2]_2(MeO)Si(CH_2)_3SH,
[(C_{13}H_{27}O—(CH_2—CH_2O)_3]_2(MeO)Si(CH_2)_3SH,
[(C_{13}H_{27}O—(CH_2—CH_2O)_4]_2(MeO)Si(CH_2)_3SH,
[(C_{13}H_{27}O—(CH_2—CH_2O)_5]_2(MeO)Si(CH_2)_3SH,
[(C_{13}H_{27}O—(CH_2—CH_2O)_6]_2(MeO)Si(CH_2)_3SH,
[(C_{14}H_{29}O—(CH_2—CH_2O)_2]_2(MeO)Si(CH_2)_3SH,
[(C_{14}H_{29}O—(CH_2—CH_2O)_3]_2(MeO)Si(CH_2)_3SH,
[(C_{14}H_{29}O—(CH_2—CH_2O)_4]_2(MeO)Si(CH_2)_3SH,
[(C_{14}H_{29}O—(CH_2—CH_2O)_5]_2(MeO)Si(CH_2)_3SH,
[(C_{14}H_{29}O—(CH_2—CH_2O)_6]_2(MeO)Si(CH_2)_3SH,
[(C_9H_{19}O—(CH_2—CH_2O)_2](EtO)_2Si(CH_2)_3SH,
[(C_9H_{19}O—(CH_2—CH_2O)_3](EtO)_2Si(CH_2)_3SH,
[(C_9H_{19}O—(CH_2—CH_2O)_4](EtO)_2Si(CH_2)_3SH,
[(C_9H_{19}O—(CH_2—CH_2O)_2](EtO)_2Si(CH_2)_3SH,
[(C_9H_{19}O—(CH_2—CH_2O)_6](EtO)_2Si(CH_2)_3SH,
[(C_{12}H_{25}O—(CH_2—CH_2O)_2](EtO)_2Si(CH_2)_3SH,
[(C_{12}H_{25}O—(CH_2—CH_2O)_3](EtO)_2Si(CH_2)_3SH,
[(C_{12}H_{25}O—(CH_2—CH_2O)_4](EtO)_2Si(CH_2)_3SH,
[(C_{12}H_{25}O—(CH_2—CH_2O)_5](EtO)_2Si(CH_2)_3SH,
[(C_{12}H_{25}O—(CH_2—CH_2O)_6](EtO)_2Si(CH_2)_3SH,
[(C_{13}H_{27}O—(CH_2—CH_2O)_2](EtO)_2Si(CH_2)_3SH,
[(C_{13}H_{27}O—(CH_2—CH_2O)_3](EtO)_2Si(CH_2)_3SH,
[(C_{13}H_{27}O—(CH_2—CH_2O)_4](EtO)_2Si(CH_2)_3SH,
[(C_{13}H_{27}O—(CH_2—CH_2O)_5](EtO)_2Si(CH_2)_3SH,
[(C_{13}H_{27}O—(CH_2—CH_2O)_6](EtO)_2Si(CH_2)_3SH,
[(C_{14}H_{29}O—(CH_2—CH_2O)_2](EtO)_2Si(CH_2)_3SH,
[(C_{14}H_{29}O—(CH_2—CH_2O)_3](EtO)_2Si(CH_2)_3SH,
[(C_{14}H_{29}O—(CH_2—CH_2O)_4](EtO)_2Si(CH_2)_3SH,
[(C_{14}H_{29}O—(CH_2—CH_2O)_5](EtO)_2Si(CH_2)_3SH,
[(C_{14}H_{29}O—(CH_2—CH_2O)_6](EtO)_2Si(CH_2)_3SH,
[(C_9H_{19}O—(CH_2—CH_2O)_2]_2(EtO)Si(CH_2)_3SH,
[(C_9H_{19}O—(CH_2—CH_2O)_3]_2(EtO)Si(CH_2)_3SH,
[(C_9H_{19}O—(CH_2—CH_2O)_4]_2(EtO)Si(CH_2)_3SH,
[(C_9H_{19}O—(CH_2—CH_2O)_5]_2(EtO)Si(CH_2)_3SH,
[(C_9H_{19}O—(CH_2—CH_2O)_6]_2(EtO)Si(CH_2)_3SH,
[(C_{12}H_{25}O—(CH_2—CH_2O)_2]_2(EtO)Si(CH_2)_3SH,
[(C_{12}H_{25}O—(CH_2—CH_2O)_3]_2(EtO)Si(CH_2)_3SH,
[(C_{12}H_{25}O—(CH_2—CH_2O)_4]_2(EtO)Si(CH_2)_3SH,
[(C_{12}H_{25}O—(CH_2—CH_2O)_5]_2(EtO)Si(CH_2)_3SH,
[(C_{12}H_{25}O—(CH_2—CH_2O)_6]_2(EtO)Si(CH_2)_3SH,
[(C_{13}H_{27}O—(CH_2—CH_2O)_2]_2(EtO)Si(CH_2)_3SH,
[(C_{13}H_{27}O—(CH_2—CH_2O)_3]_2(EtO)Si(CH_2)_3SH,
[(C_{13}H_{27}O—(CH_2—CH_2O)_4]_2(EtO)Si(CH_2)_3SH,
[(C_{13}H_{27}O—(CH_2—CH_2O)_5]_2(EtO)Si(CH_2)_3SH,
[(C_{13}H_{27}O—(CH_2—CH_2O)_6]_2(EtO)Si(CH_2)_3SH,
[(C_{14}H_{29}O—(CH_2—CH_2O)_2]_2(EtO)Si(CH_2)_3SH,
[(C_{14}H_{29}O—(CH_2—CH_2O)_3]_2(EtO)Si(CH_2)_3SH,
[(C_{14}H_{29}O—(CH_2—CH_2O)_4]_2(EtO)Si(CH_2)_3SH,
[(C_{14}H_{29}O—(CH_2—CH_2O)_5]_2(EtO)Si(CH_2)_3SH,
[(C_{14}H_{29}O—(CH_2—CH_2O)_6]_2 (EtO)Si(CH_2)_3SH,
[(C_9H_{19}O—(CH_2—CH_2O)_2]_3Si(CH_2)_3SH, [(C_9H_{19}O—(CH_2—CH_2O)_3]_3Si(CH_2)_3SH, [(C_9H_{19}O—(CH_2—CH_2O)_4]_3Si(CH_2)_3SH, [(C_9H_{19}O—(CH_2—CH_2O)_5]_3Si(CH_2)_3SH, [(C_9H_{19}O—(CH_2—CH_2O)_6]_3Si(CH_2)_3SH,
[(C_{12}H_{25}O—(CH_2—CH_2O)_2]_3Si(CH_2)_3SH,
[(C_{12}H_{25}O—(CH_2—CH_2O)_3]_3Si(CH_2)_3SH,
[(C_{12}H_{25}O—(CH_2—CH_2O)_4]_3Si(CH_2)_3SH,
[(C_{12}H_{25}O—(CH_2—CH_2O)_5]_3Si(CH_2)_3SH,
[(C_{12}H_{25}O—(CH_2—CH_2O)_6]_3Si(CH_2)_3SH,
[(C_{13}H_{27}O—(CH_2—CH_2O)_2]_3Si(CH_2)_3SH,
[(C_{13}H_{27}O—(CH_2—CH_2O)_3]_3Si(CH_2)_3SH,
[(C_{13}H_{27}O—(CH_2—CH_2O)_4]_3Si(CH_2)_3SH,
[(C_{13}H_{27}O—(CH_2—CH_2O)_5]_3Si(CH_2)_3SH,
[(C_{13}H_{27}O—(CH_2—CH_2O)_6]_3Si(CH_2)_3SH,
[(C_{14}H_{29}O—(CH_2—CH_2O)_2]_3Si(CH_2)_3SH,
[(C_{14}H_{29}O—(CH_2—CH_2O)_3]_3Si(CH_2)_3SH,
[(C_{14}H_{29}O—(CH_2—CH_2O)_4]_3Si(CH_2)_3SH,
[(C_{14}H_{29}O—(CH_2—CH_2O)_5]_3Si(CH_2)_3SH,
[(C_{14}H_{29}O—(CH_2—CH_2O)_6]_3Si(CH_2)_3SH or
HS—CH_2—CH_2—CH_2—Si(OCH_2—CH_2—)_3N.

The alcohol can be used in a fraction of 0.01% to 95%, preferably of 0.1% to 60%, more preferably of 0.1% to 40%, very preferably of 0.1% to 30%, and with greatest preference of 1% to 5%, by weight, based on the total weight of bis(alkoxysilylorganyl) polysulphides and alcohol.

The alcohol used may be a mixture of alcohols. It may have a boiling point of 50° C. to 280° C., preferably 50-150° C., and more preferably 50-120° C. The alcohol may be a primary, secondary or tertiary alcohol, alkyl ether alcohol HO—(CR$^I_2$—CR$^I_2$)—O-Alk or alkyl polyether alcohol HO—(CR$^I_2$—CR$^I_2$O)_y-Alk.

Primary, secondary or tertiary alcohols which can be used include methanol, ethanol, n-propanol, isopropanol, isobutanol, n-butanol, tert-butanol, dodecanol, tetradecanol, hexadecanol or octadecanol.

Alkyl polyether alcohols may be the following:
HO—(CH_2—CH_2—O)_2—C_6H_{13}, HO—(CH_2—CH_2—O)_3—C_6H_{13}, HO—(CH_2—CH_2—O)_4—C_6H_{13}, HO—(CH_2—CH_2—O)_5—C_6H_{13}, HO—(CH_2—CH_2—O)_6—C_6H_{13} HO—(CH_2—CH_2—O)_7—C_6H_{13}, HO—(CH_2—CH_2—O)_8—C_6H_{13}, HO—(CH_2—CH_2—O)_9—C_6H_{13}, HO—(CH_2—CH_2—O)_2—C_{10}H_{21}, HO—(CH_2—CH_2—O)_3—C_{10}H_{21}, HO—(CH_2—CH_2—O)_4—C_{10}H_{21}, HO—(CH_2—CH_2—O)_5—C_{10}H_{21}, HO—(CH_2—CH_2—O)_6—C_{10}H_{21}, HO—(CH_2—CH_2—O)_7—C_{10}H_{21}, HO—(CH_2—CH_2—O)_8—C_{10}H_{21}, HO—(CH_2—CH_2—O)_9—C_{10}H_{21}, HO—(CH_2—CH_2—O)_2—C_{13}H_{27}, HO—(CH_2—CH_2—O)_3—C_{13}H_{27}, HO—(CH_2—CH_2—O)_4—C_{13}H_{27}, HO—(CH_2—CH_2—O)_5—C_{13}H_{27}, HO—(CH_2—CH_2—O)_6—C_{13}H_{27}, HO—(CH_2—CH_2—O)_7—C_{13}H_{27}, HO—(CH_2—CH_2—O)_8—C_{13}H_{27}, HO—(CH_2—CH_2—O)_9—C_{13}H_{27}, HO—(CH_2—CH_2—O)_2—C_{14}H_{29}, HO—(CH_2—CH_2—O)_3—C_{14}H_{29}, HO—(CH_2—CH_2—O)_4—C_{14}H_{29}, HO—(CH_2—CH_2—O)_5—C_{14}H_{29}, HO—(CH_2—CH_2—O)_6—C_{14}H_{29}, HO—(CH_2—CH_2—O)_7—C_{14}H_{29}, HO—(CH_2—CH_2—O)_8—C_{14}H_{29}, HO—(CH_2—CH_2—O)_9—C_{14}H_{29}, HO—(CH_2—CH_2—O)_2—C_{15}H_{31}, HO—(CH_2—CH_2—O)_3—

$C_{15}H_{31}$, HO—$(CH_2$—$CH_2$—O$)_4$—$C_{15}H_{31}$, HO—$(CH_2$—$CH_2$—O$)_5$—$C_{15}H_{31}$, HO—$(CH_2$—$CH_2$—O$)_6$—$C_{15}H_{31}$, HO—$(CH_2$—$CH_2$—O$)_7$—$C_{15}H_{31}$, HO—$(CH_2$—$CH_2$—O$)_8$—$C_{15}H_{31}$ or HO—$(CH_2$—$CH_2$—O$)_9$—$C_{15}H_{31}$.

The reaction can be carried out preferably with exclusion of air and water.

Prior to, during or at the end of the reaction it is possible to add additives to the reaction mixture. The additives may prolong the service life of the catalysts employed, simplify or enhance handling of the catalysts, increase the reusability of the catalysts or improve the economics of the process.

Additives may be organosulphur compounds, titanium alkoxylates, amines, water, organic or inorganic acids or bases, or mixtures of the aforementioned compounds. They may also be carboxylic acids, DMSO, monoalkylamines, dialkylamines or trialkylamines. Additives may be $Ti(OC_4H_9)_4$ or $Ti(OC_3H_7)_4$.

The reaction mixture may include by-products and/or impurities which have come about in an upstream process step during the preparation of the bis(alkoxysilylorganyl) polysulphides. The by-products and/or impurities may reduce the complexity and the cost and inconvenience of the overall process encompassing bis(alkoxysilylorganyl) polysulphide preparation and hydrogenation. The presence of by-products and/or impurities may be the consequence of omitting a separation step during the working-up of the bis (alkoxysilylorganyl) polysulphides used as starting material for the hydrogenation. Possible by-products and/or impurities include alkali metal halides, preferably sodium chloride and potassium chloride.

The hydrogenation can be carried out under a hydrogen overpressure of 5 to 250 bar, preferably 5 to 99 bar, more preferably 5 to 55 bar, very preferably 5 to 40 bar.

The hydrogenation may be carried out at a temperature of 50 to 250° C., preferably 75 to 189° C., more preferably 100 to 175° C., very preferably 110 to 160° C.

The time for the hydrogenation reaction may amount to less than 360 minutes, preferably less than 300 minutes, more preferably less than 240 minutes, very preferably less than 180 minutes.

The doping component of the doped metal catalyst may be at least one metal and/or at least one metal compound. The doped metal catalyst may be a mixture composed of at least one substance from the group consisting of iron, iron compound, nickel, nickel compound, palladium, palladium compound, osmium, osmium compound, ruthenium, ruthenium compound, rhodium, rhodium compound, iridium and iridium compound and of at least one metal and/or at least one metal compound, which independently of one another may be present in elemental, alloyed, chemically bonded or physically mixed form.

The substance from the group consisting of iron, iron compound, nickel, nickel compound, palladium, palladium compound, osmium, osmium compound, ruthenium, ruthenium compound, rhodium, rhodium compound, iridium and iridium compound is different from the doping component of the doped metal catalyst.

The doping component of the doped metal catalyst may be composed of at least one metal and/or at least one metal compound that differs from the substance from the group consisting of iron, iron compound, nickel, nickel compound, palladium, palladium compound, osmium, osmium compound, ruthenium, ruthenium compound, rhodium, rhodium compound, iridium and iridium compound.

The doping component may have been applied to the doped metal catalyst by absorption, adsorption or deposition. The doped metal catalyst may be a mixture composed of at least two metals and/or metal compounds, the catalytically active species being formed only during the hydrogenation, from precursors.

The doping component for the doped metal catalysts may comoprise alkali metals or alkali metal compounds, preferably based on Li, Na, K or Rb, alkaline earth metals or alkaline earth metal compounds, preferably based on Be, Mg, Ca, Sr or Ba, elements from main group 3 and compounds of main group 3, preferably based on B, Al, Ga or In, elements from main group 4 and compounds of main group 4, preferably based on C, Si, Ge, Sn or Pb, elements from main group 5 and compounds of main group 5, preferably based on N, P, As or Sb, elements from main group 6 and compounds of main group 6, preferably based on O, S, Se or Te, elements from main group 7 and compounds of main group 7, preferably based on F, Cl, Br or I, transition group elements and compounds of transition group elements, preferably based on Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn or Cd, elements of the lanthanoid group and compounds of the lanthanoids, preferably based on lanthanum, cerium, praseodymium, neodymium, samarium, europium, gadolinium, ytterbium or lutetium.

The doping component may be free from ruthenium oxide, from nickel oxide and from palladium oxide. The doping component may be different from the catalyst support material. A preferred doping component is a hydride, oxide, halide, for example fluoride, chloride, bromide or iodide, sulphide or nitride.

The doped metal catalysts may preferably comprise as substance hydrides, oxides, halides, sulphides and/or nitrides of Fe, Ni, Ru, Rh, Pd, Os or Ir.

The doped metal catalysts may preferably comprise as doping component hydrides, oxides, halides, sulphides and/or nitrides of Fe, Ni, Ru, Rh, Pd, Os or Ir. The doping component may preferably comprise oxides, for example nickel oxide, iron oxide, ruthenium oxide, rhodium oxide, osmium oxide, iridium oxide and palladium oxide. It may preferably comprise sulphides, for example nickel sulphide, iron sulphide, ruthenium sulphide, rhodium sulphide, osmium sulphide, iridium sulphide and palladium sulphide.

The doped metal catalysts may be porous skeletal or activated metal catalysts of the Raney type which have been doped with transition metals and/or transition metal compounds, molybdenum for example. The doped metal catalysts may preferably be activated nickel metal catalysts of the Raney type that have been doped with transition metals and/or transition metal compounds, molybdenum for example.

Examples of doped metal catalysts which can be used are the catalysts BK 111 W (activated, nickel-based metal catalyst doped with <5% by weight molybdenum) and BK 113 W (activiated, nickel-based metal catalyst doped with <5% by weight molybdenum) from Degussa AG.

The weight fraction of the doping component (present in elemental form or as a chemical compound), based on the weight of the doped metal catalyst, can be 0.00001% to 80%, preferably 0.0001% to 50%, more preferably 0.001% to 15%, very preferably 0.01% to 7.5%, by weight.

The doped component may form a physical mixture with the substance of the doped metal catalyst and/or its precursors and/or the catalyst support material. The doping component may form a chemical compound with the substance of the doped metal catalyst and/or its precursors and/or the catalyst support material.

The doping component may form an alloy with the substance of the doped metal catalyst and/or its precursors. It may also form mixed crystals with the substance of the doped metal catalyst and/or its precursors.

The doped metal catalyst may be composed of finely divided, unsupported, activated metals and/or metal compounds. It may have been applied to one of the known and customary catalyst support materials, such as diatomaceous earth (kieselguhr), carbon, silica, activated carbons, alumina or aluminosilicate.

The substance of the doped metal catalyst and also the doping component may be applied together, separately or successively to one of the known and customary catalyst support materials, such as diatomaceous earth (kieselguhr), carbon, silica, activated carbons, alumina or aluminosilicate.

The doped metal catalysts may be used in solid form, in suspension or embedded in waxes or oils for the reaction. The catalyst concentration, based on the molar amount of the substance of the doped metal catalyst, may be 0.0001 to 1 mmol per g of bis(alkoxysilylorganyl) polysulphide.

For nickel and iron the concentration, based on the amount of substance of the doped metal catalyst, may be preferably from 0.001 to 1 mmol, more preferably 0.01 to 1 mmol, very preferably 0.05 to 0.5 mmol, per g of bis(alkoxysilylorganyl) polysulphide.

For ruthenium, rhodium, osmium or iridium the concentration, based on the amount of substance of the doped metal catalyst, may be preferably from 0.0001 to 1 mmol, more preferably 0.005 to 0.5 mmol, very preferably 0.005 to 0.1 mmol, per g of bis(alkoxysilylorganyl) polysulphide.

For palladium the concentration, based on the amount of substance of the doped metal catalyst, may be preferably from 0.0001 to 1 mmol, more preferably 0.005 to 1 mmol, very preferably 0.01 to 0.5 mmol, per g of bis(alkoxysilylorganyl) polysulphide.

Parameters serving for comparison of the rate of hydrogenolysis at a given temperature T and a constant pressure p may be the weight conversion, which can be expressed quantitatively by the relationship "product in g" per "mmol of substance of the doped metal catalyst" per "minute". As further parameters for comparing the rate of the hydrogenolysis at a given temperature T and a constant pressure p it is possible to employ the molar conversion, which can be expressed quantitatively by the relationship "product in mmol" per "mmol of substance of the doped metal catalyst" per "minute".

If it is possible to raise the conversion at lower temperatures and/or lower pressures, this constitutes a substantial improvement in terms of ecology, energy and economics. The weight conversion can be 0.001 to 10 g of mercaptoorganyl (alkoxysilane) per mmol of doped metal or metal compound per minute. The molar conversion can be 0.001 to 50 mmol of mercaptoorganyl(alkoxysilane) per mmol of doped metal per minute.

For the substance of the doped metal catalyst as nickel, ruthenium, rhodium, iridium or palladium, the weight conversion can be preferably 0.001 to 10 g, more preferably 0.01 to 10 g, very preferably 0.1 to 10 g of mercapto-organyl (alkoxysilane) per mmol of doped metal per minute. For the substance of the doped metal catalyst as nickel, ruthenium, rhodium, iridium or palladium the molar conversion can be preferably 0.001 to 50 mmol, preferably 0.01 to 40 mmol, more preferably 0.05 to 30 mmol, very preferably 0.1 to 20 mmol of mercaptoorganyl(alkoxysilane) per mmol of doped metal per minute.

Using the process of the invention it is possible to convert more than 80%, preferably more than 83%, more preferably more than 86%, very preferably more than 90%, by weight, of the bis(alkoxysilylorganyl) polysulphides employed into a mercaptoorganyl(alkoxysilane). With the process of the invention the relative fraction (mol %) of the bis(alkoxysilylorganyl) monosulphide present in the bis(alkoxysilylorganyl) polysulphides employed may remain constant. The relative fraction of the bis(alkoxysilyl-organyl) monosulphide present in the reactant may be <10%, preferably <8%, more preferably <6%, very preferably <4%, by weight.

The process of the invention may be a batch process or a continuous process. In the case of the batch process it may be a slurry process or suspension process, in stirred autoclaves or Buss reactors, for example.

In the case of continuous processes the process may be a slurry process with continuous supply of gas and liquid. In the case of the continuous process it is possible to employ known reactors for gas/liquid/solid reactions. Typical representatives of fixed-bed reactors may be the trickle-bed reactor and liquid-filled reactor; for suspension reactors, the stirred tank, the bubble column and the fluidized bed.

The process of the invention has the advantage that higher conversions are obtained when using doped catalysts than when employing undoped catalysts. In comparison to the prior art (U.S. Pat. No. 6,433,206) it is possible using doped catalysts to obtain higher conversions on a metal-specific or substrate-specific basis, at milder temperatures and/or pressures. The higher conversion not only considerably improves the space-time yield but also lowers the specific energy consumption for the preparation of mercapto-organyl(alkoxysilanes) by reductive cleavage with $H_2$ from bis(alkoxysilylorganyl) polysulphides. The lower energy consumption and milder reaction conditions impose less stress on the plant, resulting in, among other things, reduced wear and maintenance expenditure. A lower energy consumption in the preparation of mercaptoorganyl(alkoxysilanes) improves the energy balance of the process and imposes less of a burden on the environment. The complexity of technical plant generally decreases as process temperatures and process pressures become lower.

EXAMPLES

Table 1 lists examples from U.S. Pat. No. 6,433,206. The polysulphanesilane used is an unspecified disulphanesilane mixture containing primarily bis(3-triethoxysilylpropyl) disulphide. No formation of by-products is described. Product analysis takes place by gas chromatography methods or techniques.

Table 2 describes, as comparative example 1, the use of an undoped palladium catalyst at 155° C. and 51 bar. In order to achieve effective comparability of the results the percentages by weight in the comparative examples in tables 1 and 2 are corrected for the alcohol fractions of the product solution (example: a 50% strength product solution of alcohol and silane contains 25% by weight mercaptosilane and 25% by weight disulphanesilane. In other words, the silane constituents of the product are 50% by weight mercaptosilane and 50% by weight disulphanesilane.).

The stated weight percentages of the silane constituents in Tables 3 and 4 are likewise corrected for the alcohol fraction of the solutions.

TABLE 1

Comparative examples as per U.S. Pat. No. 6,433,206

| No. | Temperature °C. | Pressure psig | Pressure bar | Catalyst type | Amount of catalyst g | Amount of metal based on catalyst g | Molar amount of metal employed, based on catalyst mmol | Polysulphane-silane g | EtOH g |
|---|---|---|---|---|---|---|---|---|---|
| 19 | 190 | 300 | 51 | 55% Ni/silica (G-49B) | 5 | 2.75 | 46.9 | 256 | 251 |
|  |  |  |  |  |  |  | 46.9 | 256 | 251 |
| 22 | 190 | 300 | 51 | 55% Ni/silica (G-49B) | 5 | 2.75 | 46.9 | 498 | 53 |
|  |  |  |  |  |  |  | 46.9 | 498 | 53 |
|  |  |  |  |  |  |  | 46.9 | 498 | 53 |
| 5 | 190 | 1400 | 235.2 | 5% Pd/C | 6 | 0.3 | 2.82 | 359 | 324 |
| 8 | 190 | 1400 | 235.2 | 10% Pd/C | 6 | 0.6 | 5.64 | 255 | 254 |

| No. | EtOH % by wt. | Time min | SH % by wt. | S1 % by wt. | S2 % by wt. | Polysulphide % by wt. | Ratio of silane formed to amount of catalyst metal per minute (weight conversion) g/mmol/min |
|---|---|---|---|---|---|---|---|
| 19 | 49.5 | 60 | 24.9 | 4.33 | 16.5 | 1.5 | 0.045 |
|  | 49.5 | 120 | 44.5 | 5.5 | 0 | 0 | 0.040 |
| 22 | 9.6 | 60 | 18.2 | 7.6 | 51.4 | 5.7 | 0.036 |
|  | 9.6 | 120 | 35.3 | 7.85 | 39.1 | 2.5 | 0.035 |
|  | 9.6 | 180 | 55.9 | 8 | 19.4 | 0 | 0.037 |
| 5 | 47.44 | 60 | 14.1 | 7.8 | 61.8 | 7.8 | 0.30 |
| 8 | 49.90 | 60 | 14.2 | 7.2 | 54.9 | 7.8 | 0.11 |

TABLE 2

Comparative example 1

| Temperature °C. | Pressure bar | Catalyst type | Mass of catalyst mg | Amount of metal based on catalyst mg | Amount of metal based on catalyst mmol | Polysulphane-silane g | EtOH g | EtOH % by wt. | Time min | SH % by wt. | S2 % by wt. | S3 % by wt. | Polysulphide % by wt. | Ratio of silane formed to amount of catalyst metal per minute (weight conversion) g/mmol/min |
|---|---|---|---|---|---|---|---|---|---|---|---|---|---|---|
| 155 | 51 | E105Y/W 5% Pd | 20.2 | 1.01 | 0.009 | 0.28 | 4.52 | 94 | 211 | 95.8 | 4.2 | 0 | 0 | 0.136 |

Tables 3 and 4 summarize the inventive examples based on a disulphanesilane (Si 266=commercial product from Degussa AG=[bis(triethoxysilylpropyl)disulphide]). In an apparatus consisting of 8 parallel, oilbath-heated autoclaves with a reactor volume of 20 ml each and equipped with anchor-shaped magnetic stirrers which rotate at 1300 rpm on a fixed shaft located in the centre of the reactor, Si 266 is catalytically hydrogenated in accordance with the conditions and relationships shown in tables 3 and 4.

The reaction is ended after the stated times. The product composition is determined by means of $^1$H NMR and the conversion is determined from the product composition.

The average chain length of the polysulphane mixture, determined by HPLC, is 2.14 (only the HPLC-determined mean value of S2-S14 is taken into account). The average molecular weight which results for Si 266 is 460 g/mol.

The product composition columns in Tables 3 and 4 take account only of the following components: 3-mercaptopropyl (triethoxysilane), bis(triethoxysilylpropyl) disulphide, bis (triethoxysilylpropyl)trisulphide and bis(triethoxysilylpropyl) polysulphide (Sx mit x>3).

Bis(triethoxysilylpropyl) monosulphide and 3-chloro-propyl(triethoxysilane) are disregarded.

TABLE 3

| No. | Temperature °C. | Pressure bar | Catalyst type | Mass of catalyst mg | Amount of metal based on catalyst mg | Amount of metal based on catalyst mmol | Polysulphane-silane g | EtOH g | EtOH wt. % | Time min |
|---|---|---|---|---|---|---|---|---|---|---|
| 1 | 167 | 50 | T-8027 | 50.20 | 26.10 | 0.44 | 5.00 | 1.30 | 20.6 | 139.00 |
| 2 | 159 | 50 | T-8027 | 30.60 | 15.91 | 0.27 | 5.00 | 1.30 | 20.6 | 132.00 |
| 3 | 161 | 50 | T-8027 | 50.20 | 26.10 | 0.44 | 4.00 | 2.50 | 38.5 | 132.00 |
| 4 | 167 | 50 | T-8027 | 31.00 | 16.12 | 0.27 | 4.00 | 2.50 | 38.5 | 122.00 |

| No. | SH wt. % | S2 wt. % | S3 wt. % | Polysulphide wt. % | Ratio of silane formed to amount of catalyst metal per minute (weight conversion) g/mmol/min | Ratio of silane formed to amount of catalyst metal per minute (molar conversion) mmol/mmol/min |
|---|---|---|---|---|---|---|
| 1 | 75.60 | 24.40 | 0.00 | 0.00 | 0.061 | 0.257 |
| 2 | 38.90 | 58.60 | 2.50 | 0.00 | 0.054 | 0.228 |
| 3 | 82.70 | 17.30 | 0.00 | 0.00 | 0.056 | 0.237 |
| 4 | 50.20 | 49.80 | 0.00 | 0.00 | 0.060 | 0.252 |

TABLE 4

| No. | Temperature °C. | Pressure bar | Catalyst type | Mass of catalyst mg | Amount of metal based on catalyst mg | Amount of metal based on catalyst mmol | Polysulphane-silane g | EtOH g | EtOH wt. % | Time min |
|---|---|---|---|---|---|---|---|---|---|---|
| 5 | 152 | 50 | E 105 XRS/W 5% Pd; S doped | 20.1 | 1.005 | 0.009 | 0.28 | 4.52 | 0.94 | 137 |
| 6 | 126 | 50 | CE 101 XR/W 5% Pd + 1% Sn | 20 | 1 | 0.009 | 0.28 | 4.52 | 0.94 | 55 |
| 7 | 154 | 50 | CE 105 XR/W 5% Pd + 0.5% Mo | 20.8 | 1.04 | 0.010 | 0.28 | 4.52 | 0.94 | 80 |

| No. | SH wt. % | S2 wt. % | S3 wt. % | Polysulphide wt. % | Ratio of silane formed to amount of catalyst metal per minute (weight conversion) g/mmol/min | Ratio of silane formed to amount of catalyst metal per minute (molar conversion) mmol/mmol/min |
|---|---|---|---|---|---|---|
| 5 | 100 | 0 | 0 | 0 | 0.220 | 0.923 |
| 6 | 100 | 0 | 0 | 0 | 0.550 | 2.312 |
| 7 | 96 | 4 | 0 | 0 | 0.349 | 1.467 |

The abbreviations in the tables have the following meanings:
SH=3-mercaptopropyl(triethoxysilane),
S2=bis(triethoxysilylpropyl) disulphide,
S3=bis(triethoxysilylpropyl) trisulphide,
polysulphide=bis(triethoxysilylpropyl) polysulphide (Sx with x>3).

The catalysts with the abbreviated designations:
E 105 Y/W 5% Pd
E 105 XRS/W 5% Pd; S doped
CE 101 XR/W 5% Pd+1% Sn
CE 105 XR/W 5% Pd+0.5% Mo are commercial products from Degussa AG which are produced by applying a noble metal component, such as palladium, to a porous support material of high surface area. The catalysts are employed in the form of free-flowing powderous solids. The stated catalysts are supported on activated carbons. The catalysts with the abbreviated designations given below contain the following amounts of active metal:

E 105 Y/W 5% Pd=5% Pd based on the dry mass of the catalyst;
E 105 XRS/W 5% Pd=5% Pd based on the dry mass of the catalyst;
CE 101 XR/W 5% Pd+1% Sn=5% Pd based on the dry mass of the catalyst;
CE 105 XR/W 5% Pd+0.5% Mo=5% Pd based on the dry mass of the catalyst.

The catalysts with the abbreviated designations given below contain the following amounts of doping component:
E 105 XRS/W 5% Pd=doped with S
CE 101 XR/W 5% Pd+1% Sn=doped with 1% Sn
CE 105 XR/W 5% Pd+0.5% Mo=doped with 0.5% Mo.

The catalysts G-49 B and T 8027 are commercial products from Süd-Chemie AG. The catalyst G-49 B contains 55% nickel and is undoped. The catalyst T 8027 contains 52% nickel and is doped with 2.4% zirconium.

The products are analysed using a DRX 500 NMR instrument from Bruker, in accordance with the operating procedures and rules that are known to the skilled person. The measurement frequencies are 99.35 MHz for $^{29}$Si nuclei and 500.13 MHz for $^1$H nuclei. The reference used is tetramethylsilane (TMS).

Bis(alkoxysilylorganyl) polysulphides and mixtures thereof can be analysed using GC and HPLC (U. Görl, J. Münzenberg, D. Luginsland, A. Müller Kautschuk Gummi Kunststoffe 1999, 52(9), 588, D. Luginsland Kautschuk Gummi Kunststoffe 2000, 53(1-2), 10, M. W. Backer et al., Polymer Preprints 2003, 44(1), 245). From the data set out in Tables 1 to 4 it is clear that the use of doped metal catalysts permits at least equally high conversions under more energy-sparing conditions as compared with the prior art (U.S. Pat. No. 6,433,206).

The doping of palladium with sulphur, tin or molybdenum results in conversions which are higher in some cases under more energy-saving conditions or similar conditions.

The doping of nickel with zirconium leads, for example, to an increase in conversions under more energy-sparing conditions as compared with the prior art (U.S. Pat. No. 6,433,206).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for preparing mercaptoorganyl(alkoxysilanes) comprising: hydrogenating bis(alkoxysilylorganyl) polysulphides with hydrogen in the presence of at least one alcohol and a doped metal catalyst, wherein the doped metal catalyst comprises at least one substance selected from the group consisting of: iron, iron compound, osmium, osmium compound, ruthenium, ruthenium compound, and at least one doping component, wherein said doping component comprises 0.001% to 15% by weight of said doped metal catalyst.

2. The process for preparing mercaptoorganyl(alkoxysilanes) of claim 1, wherein the weight conversion is 0.00 1 to 10 g of mercaptoorganyl(alkoxysilane) per mmol of substance of the doped metal catalyst per minute.

3. The process for preparing mercaptoorganyl(alkoxysilanes) of claim 1, wherein the molar conversion is 0.001 to 50 mmol of mercaptoorganyl(alkoxysilane) per mmol of substance of the doped metal catalyst per minute.

4. The process for preparing mercaptoorganyl(alkoxysilanes) of claim 1, wherein the hydrogenation is carried out at a temperature of between 100 and 175° C. and under a hydrogen pressure of 5 to 55 bar, and wherein said doping component comprises 0.01%-7.5% by weight of said doped metal catalyst.

5. The process of claim 1, wherein said doping component is sulphur, tin molybdenum or zirconium.

6. The process of claim 1, wherein said doped metal catalyst is formed by the absorption, adsorption or deposition of said doping component.

7. The process for preparing mercaptoorganyl(alkoxysilanes) of claim 1, wherein said mercaptoorganyl(alkoxysilanes) are compounds of the general formula (II):

W-A-SH     (II)

wherein:
W is $SiY^1Y^2Y^3$ or $Si(OCH_2—CH_2—)_3N$ and $Y^1$, $Y^2$, $Y^3$ each independently of one another may be hydroxyl (—OH), a linear, branched or cyclic hydrocarbon chain having 1-18 carbon atoms (C1-C18), a linear or branched alkyl acid group $(C_aH_{2a+1})$—C(=O)O— with a=1-25, a linear or branched alkenyl acid group $(C_bH_{2b-1})$—C(=O)O— with b=2-25, a linear or branched substituted alkyl or alkenyl acid group, an unsubstituted, halogen-substituted or alkyl-substituted cycloalkane radical having 5-12 carbon atoms, benzyl radical, a halogen-substituted or alkyl-substituted phenyl radical, a linear or branched alkoxy group, a cycloallcoxy group having 5-12 carbon atoms, a halogen-substituted or alkyl-substituted phenoxy or benzyloxy group, an alkyl ether group O—$(CR^I_2—CR^I_2)$—O-Alk or alkyl polyether group O—$(CR^I_2—CR^I_2O)_y$-Alk, with y=2-25 and wherein $R^I$ independently at each occurrence is H or an alkyl group, Alk being a linear or branched, saturated or unsaturated alkyl chain having 1-30 carbon atoms (C1-C30), and A is a linear or branched, saturated or unsaturated aliphatic, aromatic or mixedly aliphatic/aromatic divalent C1-C30 hydrocarbon chain.

8. The process for preparing a mercaptoorganyl(alkoxysilane) of claim 7, wherein said mercaptoorganyl(alkoxysilane) of formula (II) is selected from the group consisting of:
3-mercaptopropyl(trimethoxysilane), 3-mercaptopropyl (dimethoxyhydroxysilane), 3-mercaptopropyl(triethoxysilane), 3-mercaptopropyl(diethoxyhydroxysilane), 3-mercaptopropyl(diethoxymethoxysilane), 3-mercaptopropyl(tripropoxysilane), 3-mercaptopropyl(dipropoxymethoxysilane), 3-mercaptopropyl(dipropoxyhydroxysilane), 3-mercaptopropyl(tridodecanoxysilane), 3-mercaptopropyl(didodecanoxyhydroxysilane), 3-mercaptopropyl(tritetradecanoxysilane), 3-mercaptopropyl(trihexadecanoxysilane), 3-mercaptopropyl(trioctadecanoxysilane), 3-mercaptopropyl(didodecanoxy)tetradecanoxysilane, 3-mercaptopropyl(dodecanoxy)tetradecanoxy(hexadecanoxy)silane, 3-mercaptopropyl(dimethoxymethylsilane), 3-mercaptopropyl(methoxymethylhydroxysilane), 3-mercaptopropyl(methoxydimethylsilane), 3-mercaptopropyl(hydroxydimethylsilane), 3-mercaptopropyl(diethoxymethylsilane), 3-mercaptopropyl(ethoxyhydroxymethylsilane), 3-mercaptopropyl(ethoxydimethylsilane), 3-mercaptopropyl(dipropoxymethylsilane), 3-mercaptopropyl(propoxymethylhydroxysilane), 3-mercaptopropyl(propoxydimethylsilane), 3-mercaptopropyl(diisopropoxymethylsilane), 3-mercaptopropyl(isopropoxydimethylsilane), 3-mercaptopropyl(dibutoxymethylsilane), 3-mercaptopropyl(butoxydimethylsilane), 3-mercaptopropyl(disiobutoxymethylsilane), 3-mercaptopropyl(siobutoxymethylhydroxysilane), 3-mercaptopropyl(isobutoxydimethylsilane), 3-mercaptopropyl(didodecanoxymethylsilane), 3-mercaptopropyl(dodecanoxydimethylsilane), 3-mercaptopropyl(ditetradecanoxymethylsilane), 3-mercaptopropyl(tetradecanoxymethylhydroxysilane), 3-mercaptopropyl(tetradecanoxydimethylsilane), 2-mercaptoethyl(trimethoxysilane), 2-mercaptoethyl(triethoxysilane), 2-mercaptoethyl(diethoxymethoxysilane), 2-mercaptoethyl(tripropoxysilane), 2-mercaptoethyl(dipropoxymethoxysilane), 2-mercaptoethyl(tridodecanoxysilane), 2-mercaptoethyl(tritetradecanoxysilane), 2-mercaptoethyl(trihexadecanoxysilane), 2-mercaptoethyl(trioctadecanoxysilane), 2-mercaptoethyl(didodecanoxy)tetradecanoxysilan, 2-mercaptoethyl(dodecanoxy)tetradecanoxy(hexadecanoxy)silane, 2-mercaptoethyl(dimethoxymethylsilane), 2-mercaptoethyl(methoxymethylhydroxysilane), 2-mercaptoethyl(methoxydimethylsilane), 2-mercaptoethyl(diethoxymethylsilane), 2-mercaptoethyl(ethoxydimethylsilane), 2-mercaptoethyl(hydroxydimethylsilane), 1-mercaptomethyl(trimethoxysilane), 1-mercaptomethyl(triethoxysilane), 1-mercaptomethyl(diethoxymethoxysilane), 1-mercaptomethyl(diethoxyhydroxysilane), 1-mercaptomethyl(dipropoxymethoxysilane), 1-mercaptomethyl(tripropoxysilane), 1-mercaptomethyl(trimethoxysilane), 1-mercaptomethyl(dimethoxymethylsilane), 1-mercaptomethyl(methoxydimethylsilane), 1-mercaptomethyl(diethoxymethylsilane), 1-mercaptomethyl(ethoxymethylhydroxysilane), 1-mercaptomethyl(ethoxydimethylsilane), 3-mercaptobutyl(trimethoxysilane), 3-mercaptobutyl(triethoxysilane), 3-mercaptobutyl(diethoxymethoxysilane), 3-mercaptobutyl(tripropoxysilane), 3-mercaptobutyl(dipropoxymethoxysilane), 3-mercaptobutyl(dimethoxymethylsilane), 3-mercaptobutyl(diethoxymethylsilane), 3-mercaptobutyl(dimethylmethoxysilane), 3-mercaptobutyl(dimethylethoxysilane), 3-mercaptobutyl(dimethylhydroxysilane), 3-mercaptobutyl(tridodecanoxysilane), 3-mercaptobutyl(tritetradecanoxysilane), 3-mercaptobutyl(trihexadecanoxysilane), 3-mercaptobutyl(didodecanoxy)tetradecanoxysilan, 3-mercaptobutyl(dodecanoxy)tetradecanoxy(hexadecanoxy)silane, 3-mercapto-2-methyl-propyl(trimethoxysilane), 3-mercapto-2-methyl-propyl(triethoxysilane), 3-mercapto-2-methyl-propyl(diethoxymethoxysilane), 3-mercapto-2-methyl-propyl(tripropoxysilane), 3-mercapto-2-methyl-propyl(dipropoxymethoxysilane), 3-mercapto-2-methyl-propyl(tridodecanoxysilane), 3-mercapto-2-methyl-propyl(tritetradecanoxysilane), 3-mercapto-2-methyl-propyl(trihexadecanoxysilane), 3-mercapto-2-methyl-propyl(trioctadecanoxysilane), 3-mercapto-2-methyl-propyl(didodecanoxy)tetradecanoxysilane, 3-mercapto-2-methyl-propyl(dodecanoxy)tetradecanoxy(hexadecanoxy)silane, 3-mercapto-2-methyl-propyl(dimethoxymethylsilane), 3-mercapto-2-methyl-propyl(methoxydimethylsilane), 3-mercapto-2-methyl-propyl(diethoxymethylsilane), 3-mercapto-2-methyl-propyl(ethoxydimethylsilane), 3-mercapto-2-methyl-propyl(hydroxydimethylsilane), 3-mercapto-2-methyl-propyl(dipropoxymethylsilane), 3-mercapto-2-methyl-propyl(propoxydimethylsilane), 3-mercapto-2-methyl-propyl(diisopropoxymethylsilane), 3-mercapto-2-methyl-propyl(isopropoxydimethylsilane), 3-mercapto-2-methyl-propyl(dibutoxymethylsilane), 3-mercapto-2-methyl-propyl(butoxydimethylsilane), 3-mercapto-2-methyl-propyl(diisobutoxymethylsilane), 3-mercapto-2-methyl-propyl(isobutoxydimethylsilane), 3-mercapto-2-methyl-propyl(didodecanoxymethylsilane), 3-mercapto-2-methyl-propyl(dodecanoxydimethylsilane), 3-mercapto-2-methyl-propyl(ditetradecanoxymethylsilane), 3-mercapto-2-methyl-propyl(tetradecanoxydimethylsilane), $(MeO)_2Si(CH_2)_3SH$, $[(C_9H_{19}O-(CH_2-CH_2O)_2]$
$(MeO)_2Si(CH_2)_3SH$, $[(C_9H_{19}O-(CH_2-CH_2O)_3]$
$(MeO)_2Si(CH_2)_3SH$, $[(C_9H_{19}O-(CH_2-CH_2O)_4]$
$(MeO)_2Si(CH_2)_3SH$, $[(C_9H_{19}O-(CH_2-CH_2O)_5]$
$(MeO)_2Si(CH_2)_3SH$, $[(C_9H_{19}O-(CH_2-CH_2O)_6]$
$(MeO)_2Si(CH_2)_3SH$, $[(C_{12}H_{25}O-(CH_2-CH_2O)_2]$
$(MeO)_2Si(CH_2)_3SH$, $[(C_{12}H_{25}O-(CH_2-CH_2O)_3]$
$(MeO)_2Si(CH_2)_3SH$, $[(C_{12}H_{25}O-(CH_2-CH_2O)_4]$
$(MeO)_2Si(CH_2)_3SH$, $[(C_{12}H_{25}O-(CH_2-CH_2O)_5]$
$(MeO)_2Si(CH_2)_3SH$, $[(C_{12}H_{25}O-(CH_2-CH_2O)_6]$
$(MeO)_2Si(CH_2)_3SH$, $[(C_{13}H_{27}O-(CH_2-CH_2O)_2]$
$(MeO)_2Si(CH_2)_3SH$, $[(C_{13}H_{27}O-(CH_2-CH_2O)_3]$
$(MeO)_2Si(CH_2)_3SH$, $[(C_{13}H_{27}O-(CH_2-CH_2O)_4]$
$(MeO)_2Si(CH_2)_3SH$, $[(C_{13}H_{27}O-(CH_2-CH_2O)_5]$
$(MeO)_2Si(CH_2)_3SH$, $[(C_{13}H_{27}O-(CH_2-CH_2O)_6]$
$(MeO)_2Si(CH_2)_3SH$, $[(C_{14}H_{29}O-(CH_2-CH_2O)_2]$
$(MeO)_2Si(CH_2)_3SH$, $[(C_{14}H_{29}O-(CH_2-CH_2O)_3]$
$(MeO)_2Si(CH_2)_3SH$, $[(C_{14}H_{29}O-(CH_2-CH_2O)_4]$
$(MeO)_2Si(CH_2)_3SH$, $[(C_{14}H_{29}O-(CH_2-CH_2O)_5]$
$(MeO)_2Si(CH_2)_3SH$, $[(C_{14}H_{29}O-(CH_2-CH_2O)_6]$
$(MeO)Si(CH_2)_3SH$, $[(C_9H_{19}O-(CH_2-CH_2O)_2]_2$
$(MeO)Si(CH_2)_3SH$, $[(C_9H_{19}O-(CH_2-CH_2O)_3]_2$
$(MeO)Si(CH_2)_3SH$, $[(C_9H_{19}O-(CH_2-CH_2O)_4]_2$
$(MeO)Si(CH_2)_3SH$, $[(C_9H_{19}O-(CH_2-CH_2O)_5]_2$
$(MeO)Si(CH_2)_3SH$, $[(C_9H_{19}O-(CH_2-CH_2O)_6]_2$
$(MeO)Si(CH_2)_3SH$, $[(C_{12}H_{25}O-(CH_2-CH_2O)_2]_2$
$(MeO)Si(CH_2)_3SH$, $[(C_{12}H_{25}O-(CH_2-CH_2O)_3]_2$
$(MeO)Si(CH_2)_3SH$, $[(C_{12}H_{25}O-(CH_2-CH_2O)_4]_2$
$(MeO)Si(CH_2)_3SH$, $[(C_{12}H_{25}O-(CH_2-CH_2O)_5]_2$
$(MeO)Si(CH_2)_3SH$, $[(C_{12}H_{25}O-(CH_2-CH_2O)_6]_2$
$(MeO)Si(CH_2)_3SH$, $[(C_{13}H_{27}O-(CH_2-CH_2O)_2]_2$
$(MeO)Si(CH_2)_3SH$, $[(C_{13}H_{27}O-(CH_2-CH_2O)_3]_2$
$(MeO)Si(CH_2)_3SH$, $[(C_{13}H_{27}O-(CH_2-CH_2O)_4]_2$
$(MeO)Si(CH_2)_3SH$, $[(C_{13}H_{27}O-(CH_2-CH_2O)_5]_2$
$(MeO)Si(CH_2)_3SH$, $[(C_{13}H_{27}O-(CH_2-CH_2O)_6]_2$
$(MeO)Si(CH_2)_3SH$, $[(C_{14}H_{29}O-(CH_2-CH_2O)_2]_2$
$(MeO)Si(CH_2)_3SH$, $[(C_{14}H_{29}O-(CH_2-CH_2O)_3]_2$
$(MeO)Si(CH_2)_3SH$, $[(C_{14}H_{29}O-(CH_2-CH_2O)_4]_2$ (MeO)Si(CH$_2$)$_3$SH, [(C$_{14}$H$_{29}$O—(CH$_2$—CH$_2$O)$_5$]$_2$
(MeO)Si(CH$_2$)$_3$SH, [(C$_{14}$H$_{29}$O—(CH$_2$—CH$_2$O)$_6$]$_2$
(MeO)Si(CH$_2$)$_3$SH, [(C$_9$H$_{19}$O—(CH$_2$—CH$_2$O)$_2$]
(EtO)$_2$ Si(CH$_2$)$_3$SH, [(C$_9$H$_{19}$O—(CH$_2$—CH$_2$O)$_3$]
(EtO)$_2$Si(CH$_2$)$_3$SH, [(C$_9$H$_{19}$O—(CH$_2$—CH$_2$O)$_4$]
(EtO)$_2$ Si(CH$_2$)$_3$SH, [(C$_9$H$_{19}$O—(CH$_2$—CH$_2$O)$_5$]
(EtO)$_2$Si(CH$_2$)$_3$SH, [(C$_9$H$_{19}$O—(CH$_2$—CH$_2$O)$_6$]
(EtO)$_2$ Si(CH$_2$)$_3$SH, [(C$_{12}$H$_{25}$O—(CH$_2$—CH$_2$O)$_2$]
(EtO)$_2$Si(CH$_2$)$_3$SH, [(C$_{12}$H$_{25}$O—(CH$_2$—CH$_2$O)$_3$]
(EtO)$_2$Si(CH$_2$)$_3$SH, [(C$_{12}$H$_{25}$O—(CH$_2$—CH$_2$O)$_4$]
(EtO)$_2$Si(CH$_2$)$_3$SH, [(C$_{12}$H$_{25}$O—(CH$_2$—CH$_2$O)$_5$]
(EtO)$_2$Si(CH$_2$)$_3$SH, [(C$_{12}$H$_{25}$O—(CH$_2$—CH$_2$O)$_6$]
(EtO)$_2$Si(CH$_2$)$_3$SH, [(C$_{13}$H$_{27}$O—(CH$_2$—CH$_2$O)$_2$]
(EtO)$_2$Si(CH$_2$)$_3$SH, [(C$_{13}$H$_{27}$O—(CH$_2$—CH$_2$O)$_3$]
(EtO)$_2$Si(CH$_2$)$_3$SH, [(C$_{13}$H$_{27}$O—(CH$_2$—CH$_2$O)$_4$]
(EtO)$_2$Si(CH$_2$)$_3$SH, [(C$_{13}$H$_{27}$O—(CH$_2$—CH$_2$O)$_5$]
(EtO)$_2$Si(CH$_2$)$_3$SH, [(C$_{13}$H$_{27}$O—(CH$_2$—CH$_2$O)$_6$]
(EtO)$_2$Si(CH$_2$)$_3$SH, [(C$_{14}$H$_{29}$O—(CH$_2$—CH$_2$O)$_2$]
(EtO)$_2$Si(CH$_2$)$_3$SH, [(C$_{14}$H$_{29}$O—(CH$_2$—CH$_2$O)$_3$]
(EtO)$_2$Si(CH$_2$)$_3$SH, [(C$_{14}$H$_{29}$O—(CH$_2$—CH$_2$O)$_4$]
(EtO)$_2$Si(CH$_2$)$_3$SH, [(C$_{14}$H$_{29}$O—(CH$_2$—CH$_2$O)$_5$]
(EtO)$_2$Si(CH$_2$)$_3$SH, [(C$_{14}$H$_{29}$O—(CH$_2$—CH$_2$O)$_6$]
(EtO)$_2$Si(CH$_2$)$_3$SH, [(C$_9$H$_{19}$O—(CH$_2$—CH$_2$O)$_2$]$_2$
(EtO)Si(CH$_2$)$_3$SH, [(C$_9$H$_{19}$O—(CH$_2$—CH$_2$O)$_3$]$_2$(EtO)Si(CH$_2$)$_3$SH, [(C$_9$H$_{19}$O—(CH$_2$—CH$_2$O)$_4$]$_2$(EtO)Si(CH$_2$)$_3$SH, [(C$_9$H$_{19}$O—(CH$_2$—CH$_2$O)$_5$]$_2$(EtO)Si(CH$_2$)$_3$SH, [(C$_9$H$_{19}$O—(CH$_2$—CH$_2$O)$_6$]$_2$(EtO)Si(CH$_2$)$_3$SH, [(C$_{12}$H$_{25}$O—(CH$_2$—CH$_2$O)$_2$]$_2$(EtO)Si(CH$_2$)$_3$SH, [(C$_{12}$H$_{25}$O—(CH$_2$—CH$_2$O)$_3$]$_2$(EtO)Si(CH$_2$)$_3$SH, [(C$_{12}$H$_{25}$O—(CH$_2$—CH$_2$O)$_4$]$_2$(EtO)Si(CH$_2$)$_3$SH, [(C$_{12}$H$_{25}$O—(CH$_2$—CH$_2$O)$_5$]$_2$(EtO)Si(CH$_2$)$_3$SH, [(C$_{12}$H$_{25}$O—(CH$_2$—CH$_2$O)$_6$]$_2$(EtO)Si(CH$_2$)$_3$SH, [(C$_{13}$H$_{27}$O—(CH$_2$—CH$_2$O)$_2$]$_2$(EtO)Si(CH$_2$)$_3$SH, [(C$_{13}$H$_{27}$O—(CH$_2$—CH$_2$O)$_3$]$_2$(EtO)Si(CH$_2$)$_3$SH, [(C$_{13}$H$_{27}$O—(CH$_2$—CH$_2$O)$_4$]$_2$(EtO)Si(CH$_2$)$_3$SH, [(C$_{13}$H$_{27}$O—(CH$_2$—CH$_2$O)$_5$]$_2$(EtO)Si(CH$_2$)$_3$SH, [(C$_{13}$H$_{27}$O—(CH$_2$—CH$_2$O)$_6$]$_2$(EtO)Si(CH$_2$)$_3$SH, [(C$_{14}$H$_{29}$O—(CH$_2$—CH$_2$O)$_2$]$_2$(EtO)Si(CH$_2$)$_3$SH, [(C$_{14}$H$_{29}$O—(CH$_2$—CH$_2$O)$_3$]$_2$(EtO)Si(CH$_2$)$_3$SH, [(C$_{14}$H$_{29}$O—(CH$_2$—CH$_2$O)$_4$]$_2$(EtO)Si(CH$_2$)$_3$SH, [(C$_{14}$H$_{29}$O—(CH$_2$—CH$_2$O)$_5$]$_2$(EtO)Si(CH$_2$)$_3$SH, [(C$_{14}$H$_{29}$O—(CH$_2$—CH$_2$O)$_6$]$_2$(EtO)Si(CH$_2$)$_3$SH, [(C$_9$H$_{19}$O—(CH$_2$—CH$_2$O)$_2$]$_3$Si(CH$_2$)$_3$SH,
[(C$_9$H$_{19}$O—(CH$_2$—CH$_2$O)$_3$]$_3$Si(CH$_2$)$_3$SH,
[(C$_9$H$_{19}$O—(CH$_2$—CH$_2$O)$_4$]$_3$Si(CH$_2$)$_3$SH,
[(C$_9$H$_{19}$O—(CH$_2$—CH$_2$O)$_5$]$_3$Si(CH$_2$)$_3$SH,
[(C$_9$H$_{19}$O—(CH$_2$—CH$_2$O)$_6$]$_3$Si(CH$_2$)$_3$SH,
[(C$_{12}$H$_{25}$O—(CH$_2$—CH$_2$O)$_2$]$_3$Si(CH$_2$)$_3$SH,
[(C$_{12}$H$_{25}$O—(CH$_2$—CH$_2$O)$_3$]$_3$Si(CH$_2$)$_3$SH,
[(C$_{12}$H$_{25}$O—(CH$_2$—CH$_2$O)$_4$]$_3$Si(CH$_2$)$_3$SH,
[(C$_{12}$H$_{25}$O—(CH$_2$—CH$_2$O)$_5$]$_3$Si(CH$_2$)$_3$SH,
[(C$_{12}$H$_{25}$O—(CH$_2$—CH$_2$O)$_6$]$_3$Si(CH$_2$)$_3$SH,
[(C$_{13}$H$_{27}$O—(CH$_2$—CH$_2$O)$_2$]$_3$Si(CH$_2$)$_3$SH,
[(C$_{13}$H$_{27}$O—(CH$_2$—CH$_2$O)$_3$]$_3$Si(CH$_2$)$_3$SH,
[(C$_{13}$H$_{27}$O—(CH$_2$—CH$_2$O)$_4$]$_3$Si(CH$_2$)$_3$SH,
[(C$_{13}$H$_{27}$O—(CH$_2$—CH$_2$O)$_5$]$_3$Si(CH$_2$)$_3$SH,
[(C$_{13}$H$_{27}$O—(CH$_2$—CH$_2$O)$_6$]$_3$Si(CH$_2$)$_3$SH,
[(C$_{14}$H$_{29}$O—(CH$_2$—CH$_2$O)$_2$]$_3$Si(CH$_2$)$_3$SH,
[(C$_{14}$H$_{29}$O—(CH$_2$—CH$_2$O)$_3$]$_3$Si(CH$_2$)$_3$SH,
[(C$_{14}$H$_{29}$O—(CH$_2$—CH$_2$O)$_4$]$_3$Si(CH$_2$)$_3$SH,
[(C$_{14}$H$_{29}$O—(CH$_2$—CH$_2$O)$_5$]$_3$Si(CH$_2$)$_3$SH,
[(C$_{14}$H$_{29}$O—(CH$_2$—CH$_2$O)$_6$]$_3$Si(CH$_2$)$_3$SH, and
HS—CH$_2$—CH$_2$—CH$_2$—Si(OCH$_2$—CH$_2$—)$_3$N.

9. The process for preparing mercaptoorganyl(alkoxysilanes) of claim 8, wherein the hydrogenation is carried out at a temperature of between 100 and 175° C. and under a hydrogen pressure of 5 to 55 bar.

10. The process for preparing mercaptoorganyl(alkoxysilanes) of claim 9, wherein said process is carried out in a reaction mixture comprising an additive selected from the group consisting of: a titanium alkoxylate; an amine; water; and an organic or inorganic acid or base.

11. A process for preparing mercaptoorganyl(alkoxysilanes) comprising: hydrogenating bis(alkoxysilylorganyl) polysulphides with hydrogen in the presence of at least one alcohol and a doped metal catalyst, wherein the doped metal catalyst comprises at least one substance selected from the group consisting of: nickel, nickel compound, palladium, palladium compound, rhodium, rhodium compound, iridium and iridium compound, and at least one doping component.

12. The process of claim 11, wherein said doping component is sulphur, tin molybdenum or zirconium.

13. The process of claim 12, wherein said doped metal catalyst comprises palladium or a palladium compound and one or more doping components selected from the group consisting of: sulphur, tin and molybdenum.

14. The process of claim 12, wherein said doped metal catalyst comprises nickel or a nickel compound and zirconium.

15. The process of claim 11, wherein said doping component comprises 0.01%-7.5% by weight of said doped metal catalyst.

16. The process of claim 11, wherein said doped metal catalyst is formed by the absorption, adsorption or deposition of said doping component.

17. The process for preparing mercaptoorganyl(alkoxysilanes) of claim 11, wherein said mercaptoorganyl(alkoxysilanes) are compounds of the general formula (II):

$$W\text{-}A\text{-}SH \quad (II)$$

wherein:

W is $SiY^1Y^2Y^3$ or $Si(OCH_2\text{—}CH_2\text{—})_3N$ and $Y^1$, $Y^2$, $Y^3$ each independently of one another may be hydroxyl (—OH), a linear, branched or cyclic hydrocarbon chain having 1-18 carbon atoms (C1-C18), a linear or branched alkyl acid group $(C_aH_{2a+1})\text{—}C(\!\!=\!\!O)O$— with a=1-25, a linear or branched alkenyl acid group $(C_bH_{2b-1})\text{—}C(\!\!=\!\!O)O$— with b=2-25, a linear or branched substituted alkyl or alkenyl acid group, an unsubstituted, halogen-substituted or alkyl-substituted cycloalkane radical having 5-12 carbon atoms, benzyl radical, a halogen-substituted or alkyl-substituted phenyl radical, a linear or branched alkoxy group, a cycloalkoxy group having 5-12 carbon atoms, a halogen-substituted or alkyl-substituted phenoxy or benzyloxy group, an alkyl ether group O—(CR$^I_2$—CR$^I_2$)—O-Alk or alkyl polyether group O—(CR$^I_2$—CR$^I_2$O)$_y$-Alk, with y=2-25 and wherein R$^I$ independently at each occurrence is H or an alkyl group, Alk being a linear or branched, saturated or unsaturated ailcyl chain having 1-30 carbon atoms (C1-C30), and A is a linear or branched, saturated or unsaturated aliphatic, aromatic or mixedly aliphatic/aromatic divalent C1-C30 hydrocarbon chain.

18. The process for preparing a mercaptoorganyl(alkoxysilane) of claim 17, wherein said mercaptoorganyl(alkoxysilane) of formula (II) is selected from the group consisting of:
3-mercaptopropyl(trimethoxysilane), 3-mercaptopropyl (dimethoxyhydroxysilane), 3-mercaptopropyl(triethoxysilane), 3-mercaptopropyl(diethoxyhydroxysilane), 3-mercaptopropyl(diethoxymethoxysilane), 3-mercaptopropyl(tripropoxysilane), 3-mercaptopropyl(dipropoxymethoxysilane), 3-mercaptopropyl(dipropoxyhydroxysilane), 3-mercaptopropyl(tridodecanoxysilane), 3-mercaptopropyl(didodecanoxyhydroxysilane), 3-mercaptopropyl(tritetradecanoxysilane), 3-mercaptopropyl(trihexadecanoxysilane), 3-mercaptopropyl(trioctadecanoxysilane), 3-mercaptopropyl(didodecanoxy) tetradecanoxysilane, 3-mercaptopropyl(dodecanoxy) tetradecanoxy(hexadecanoxy)silane, 3-mercaptopropyl (dimethoxymethylsilane), 3-mercaptopropyl (methoxymethylhydroxysilane), 3-mercaptopropyl (methoxydimethylsilane), 3-mercaptopropyl (hydroxydimethylsilane), 3-mercaptopropyl (diethoxymethylsilane), 3-mercaptopropyl (ethoxyhydroxymethylsilane), 3-mercaptopropyl (ethoxydimethylsilane), 3-mercaptopropyl (dipropoxymethylsilane), 3-mercaptopropyl (propoxymethylhydroxysilane), 3-mercaptopropyl (propoxydimethylsilane), 3-mercaptopropyl (diisopropoxymethylsilane), 3-mercaptopropyl (isopropoxydimethylsilane), 3-mercaptopropyl (dibutoxymethylsilane), 3-mercaptopropyl (butoxydimethylsilane), 3-mercaptopropyl (disiobutoxymethylsilane), 3-mercaptopropyl (siobutoxymethylhydroxysilane), 3-mercaptopropyl (isobutoxydimethylsilane), 3-mercaptopropyl (didodecanoxymethylsilane), 3-mercaptopropyl (dodecanoxydimethylsilane), 3-mercaptopropyl (ditetradecanoxymethylsilane), 3-mercaptopropyl (tetradecanoxymethylhydroxysilane), 3-mercaptopropyl(tetradecanoxydimethylsilane), 2-mercaptoethyl(trimethoxysilane), 2-mercaptoethyl (triethoxysilane), 2-mercaptoethyl(diethoxymethoxysilane), 2-mercaptoethyl(tripropoxysilane), 2-mercaptoethyl(dipropoxymethoxysilane), 2-mercaptoethyl (tridodecanoxysilane), 2-mercaptoethyl (tritetradecanoxysilane), 2-mercaptoethyl (trihexadecanoxysilane), 2-mercaptoethyl (trioctadecanoxysilane), 2-mercaptoethyl (didodecanoxy)tetradecanoxysilan, 2-mercaptoethyl (dodecanoxy)tetradecanoxy(hexadecanoxy)silane, 2-mercaptoethyl(dimethoxymethylsilane), 2-mercaptoethyl(methoxymethylhydroxysilane), 2-mercaptoethyl (methoxydimethylsilane), 2-mercaptoethyl(diethoxymethylsilane), 2-mercaptoethyl(ethoxydimethylsilane), 2-mercaptoethyl(hydroxydimethylsilane), 1-mercaptomethyl(trimethoxysilane), 1-mercaptomethyl(triethoxysilane), 1-mercaptomethyl(diethoxymethoxysilane), 1-mercaptomethyl(diethoxyhydroxysilane), 1-mercaptomethyl(dipropoxymethoxysilane), 1-mercaptomethyl(tripropoxysilane), 1-mercaptomethyl(trimethoxysilane), 1-mercaptomethyl(dimethoxymethylsilane), 1-mercaptomethyl(methoxydimethylsilane), 1-mercaptomethyl(diethoxymethylsilane), 1-mercaptomethyl(ethoxymethylhydroxysilane), 1-mercaptomethyl(ethoxydimethylsilane), 3-mercaptobutyl(trimethoxysilane), 3-mercaptobutyl(triethoxysilane), 3-mercaptobutyl(diethoxymethoxysilane), 3-mercaptobutyl(tripropoxysilane), 3-mercaptobutyl(dipropoxymethoxysilane), 3-mercaptobutyl(dimethoxyethylsilane), 3-mercaptobutyl(diethoxymethylsilane), 3-mercaptobutyl(dimethylmethoxysilane), 3-mercaptobutyl(dimethylethoxysilane), 3-mercaptobutyl(dimethylhydroxysilane), 3-mercaptobutyl(tridodecanoxysilane), 3-mercaptobutyl(tritetradecanoxysilane), 3-mercaptobutyl(trihexadecanoxysilane), 3-mercaptobutyl(didodecanoxy)tetradecanoxysilan, 3-mercaptobutyl(dodecanoxy)tetradecanoxy(hexadecanoxy)silane, 3-mercapto-2-methyl-propyl(trimethoxysilane), 3-mercapto-2-methyl-propyl(triethoxysilane), 3-mercapto-2-methyl-propyl(diethoxymethoxysilane), 3-mercapto-2-methyl-propyl(tripropoxysilane), 3-mercapto-2-methyl-propyl(dipropoxymethoxysilane), 3-mercapto-2-methyl-propyl(tridodecanoxysilane), 3-mercapto-2-methyl-propyl(tritetradecanoxysilane), 3-mercapto-2-methyl-propyl(trihexadecanoxysilane), 3-mercapto-2-methyl-propyl(trioctadecanoxysilane), 3-mercapto-2-methyl-propyl(didodecanoxy)tetradecanoxysilane, 3-mercapto-2-methyl-propyl(dodecanoxy)tetradecanoxy(hexadecanoxy)silane, 3-mercapto-2-methyl-propyl(dimethoxymethylsilane), 3-mercapto-2-methyl-propyl(methoxydimethylsilane), 3-mercapto-2-methyl-propyl(diethoxymethylsilane), 3-mercapto-2-methyl-propyl(ethoxydimethylsilane), 3-mercapto-2-methyl-propyl(hydroxydimethylsilane), 3-mercapto-2-methyl-propyl(dipropoxymethylsilane), 3-mercapto-2-methyl-propyl(propoxydimethylsilane), 3-mercapto-2-methyl-propyl(diisopropoxymethylsilane), 3-mercapto-2-methyl-propyl(isopropoxydimethylsilane), 3-mercapto-2-methyl-propyl(dibutoxymethylsilane), 3-mercapto-2-methyl-propyl(butoxydimethylsilane), 3-mercapto-2-methyl-propyl(diisobutoxymethylsilane), 3-mercapto-2-methyl-propyl(isobutoxydimethylsilane), 3-mercapto-2-methyl-propyl(didodecanoxymethylsilane), 3-mercapto-2-methyl-propyl(dodecanoxydimethylsilane), 3-mercapto-2-methyl-propyl(ditetradecanoxymethylsilane), 3-mercapto-2-methyl-propyl(tetradecanoxydimethylsilane), $(MeO)_2Si(CH_2)_3SH$, $[(C_9H_{19}O-(CH_2-CH_2O)_2]$
$(MeO)_2Si(CH_2)_3SH$, $[(C_9H_{19}O-(CH_2-CH_2O)_3]$
$(MeO)_2Si(CH_2)_3SH$, $[(C_9H_{19}O-(CH_2-CH_2O)_4]$
$(MeO)_2Si(CH_2)_3SH$, $[(C_9H_{19}O-(CH_2-CH_2O)_5]$
$(MeO)_2Si(CH_2)_3SH$, $[(C_9H_{19}O-(CH_2-CH_2O)_6]$
$(MeO)_2Si(CH_2)_3SH$, $[(C_{12}H_{25}O-(CH_2-CH_2O)_2]$
$(MeO)_2Si(CH_2)_3SH$, $[(C_{12}H_{25}O-(CH_2-CH_2O)_3]$
$(MeO)_2Si(CH_2)_3SH$, $[(C_{12}H_{25}O-(CH_2-CH_2O)_4]$
$(MeO)_2Si(CH_2)_3SH$, $[(C_{12}H_{25}O-(CH_2-CH_2O)_5]$
$(MeO)_2Si(CH_2)_3SH$, $[(C_{12}H_{25}O-(CH_2-CH_2O)_6]$
$(MeO)_2Si(CH_2)_3SH$, $[(C_{13}H_{27}O-(CH_2-CH_2O)_2]$
$(MeO)_2Si(CH_2)_3SH$, $[(C_{13}H_{27}O-(CH_2-CH_2O)_3]$
$(MeO)_2Si(CH_2)_3SH$, $[(C_{13}H_{27}O-(CH_2-CH_2O)_4]$
$(MeO)_2Si(CH_2)_3SH$, $[(C_{13}H_{27}O-(CH_2-CH_2O)_5]$
$(MeO)_2Si(CH_2)_3SH$, $[(C_{13}H_{27}O-(CH_2-CH_2O)_6]$
$(MeO)_2Si(CH_2)_3SH$, $[(C_{14}H_{29}O-(CH_2-CH_2O)_2]$
$(MeO)_2Si(CH_2)_3SH$, $[(C_{14}H_{29}O-(CH_2-CH_2O)_3]$
$(MeO)_2Si(CH_2)_3SH$, $[(C_{14}H_{29}O-(CH_2-CH_2O)_4]$
$(MeO)_2Si(CH_2)_3SH$, $[(C_{14}H_{29}O-(CH_2-CH_2O)_5]$
$(MeO)_2Si(CH_2)_3SH$, $[(C_{14}H_{29}O-(CH_2-CH_2O)_6]$
$(MeO)Si(CH_2)_3SH$, $[(C_9H_{19}O-(CH_2-CH_2O)_2]_2$
$(MeO)Si(CH_2)_3SH$, $[(C_9H_{19}O-(CH_2-CH_2O)_3]_2$
$(MeO)Si(CH_2)_3SH$, $[(C_9H_{19}O-(CH_2-CH_2O)_4]_2$
$(MeO)Si(CH_2)_3SH$, $[(C_9H_{19}O-(CH_2-CH_2O)_5]_2$
$(MeO)Si(CH_2)_3SH$, $[(C_9H_{19}O-(CH_2-CH_2O)_6]_2$
$(MeO)Si(CH_2)_3SH$, $[(C_{12}H_{25}O-(CH_2-CH_2O)_2]_2$
$(MeO)Si(CH_2)_3SH$, $[(C_{12}H_{25}O-(CH_2-CH_2O)_3]_2$
$(MeO)Si(CH_2)_3SH$, $[(C_{12}H_{25}O-(CH_2-CH_2O)_4]_2$
$(MeO)Si(CH_2)_3SH$, $[(C_{12}H_{25}O-(CH_2-CH_2O)_5]_2$
$(MeO)Si(CH_2)_3SH$, $[(C_{12}H_{25}O-(CH_2-CH_2O)_6]_2$
$(MeO)Si(CH_2)_3SH$, $[(C_{13}H_{27}O-(CH_2-CH_2O)_2]_2$
$(MeO)Si(CH_2)_3SH$, $[(C_{13}H_{27}O-(CH_2-CH_2O)_3]_2$
$(MeO)Si(CH_2)_3SH$, $[(C_{13}H_{27}O-(CH_2-CH_2O)_4]_2$
$(MeO)Si(CH_2)_3SH$, $[(C_{13}H_{27}O-(CH_2-CH_2O)_5]_2$
$(MeO)Si(CH_2)_3SH$, $[(C_{13}H_{27}O-(CH_2-CH_2O)_6]_2$
$(MeO)Si(CH_2)_3SH$, $[(C_{14}H_{29}O-(CH_2-CH_2O)_2]_2$
$(MeO)Si(CH_2)_3SH$, $[(C_{14}H_{29}O-(CH_2-CH_2O)_3]_2$
$(MeO)Si(CH_2)_3SH$, $[(C_{14}H_{29}O-(CH_2-CH_2O)_4]_2$

| | |
|---|---|
| (MeO)Si(CH$_2$)$_3$SH, | [(C$_{14}$H$_{29}$O—(CH$_2$—CH$_2$O)$_5$]$_2$ |
| (MeO)Si(CH$_2$)$_3$SH, | [(C$_{14}$H$_{29}$O—(CH$_2$—CH$_2$O)$_6$]$_2$ |
| (MeO)Si(CH$_2$)$_3$SH, | [(C$_9$H$_{19}$O—(CH$_2$—CH$_2$O)$_2$] |
| (EtO)$_2$ Si(CH$_2$)$_3$SH, | [(C$_9$H$_{19}$O—(CH$_2$—CH$_2$O)$_3$] |
| (EtO)$_2$Si(CH$_2$)$_3$SH, | [(C$_9$H$_{19}$O—(CH$_2$—CH$_2$O)$_4$] |
| (EtO)$_2$ Si(CH$_2$)$_3$SH, | [(C$_9$H$_{19}$O—(CH$_2$—CH$_2$O)$_5$] |
| (EtO)$_2$Si(CH$_2$)$_3$SH, | [(C$_9$H$_{19}$O—(CH$_2$—CH$_2$O)$_6$] |
| (EtO)$_2$ Si(CH$_2$)$_3$SH, | [(C$_{12}$H$_{25}$O—(CH$_2$—CH$_2$O)$_2$] |
| (EtO)$_2$Si(CH$_2$)$_3$SH, | [(C$_{12}$H$_{25}$O—(CH$_2$—CH$_2$O)$_3$] |
| (EtO)$_2$Si(CH$_2$)$_3$SH, | [(C$_{12}$H$_{25}$O—(CH$_2$—CH$_2$O)$_4$] |
| (EtO)$_2$Si(CH$_2$)$_3$SH, | [(C$_{12}$H$_{25}$O—(CH$_2$—CH$_2$O)$_5$] |
| (EtO)$_2$Si(CH$_2$)$_3$SH, | [(C$_{12}$H$_{25}$O—(CH$_2$—CH$_2$O)$_6$] |
| (EtO)$_2$Si(CH$_2$)$_3$SH, | [(C$_{13}$H$_{27}$O—(CH$_2$—CH$_2$O)$_2$] |
| (EtO)$_2$Si(CH$_2$)$_3$SH, | [(C$_{13}$H$_{27}$O—(CH$_2$—CH$_2$O)$_3$] |
| (EtO)$_2$Si(CH$_2$)$_3$SH, | [(C$_{13}$H$_{27}$O—(CH$_2$—CH$_2$O)$_4$] |
| (EtO)$_2$Si(CH$_2$)$_3$SH, | [(C$_{13}$H$_{27}$O—(CH$_2$—CH$_2$O)$_5$] |
| (EtO)$_2$Si(CH$_2$)$_3$SH, | [(C$_{13}$H$_{27}$O—(CH$_2$—CH$_2$O)$_6$] |
| (EtO)$_2$Si(CH$_2$)$_3$SH, | [(C$_{14}$H$_{29}$O—(CH$_2$—CH$_2$O)$_2$] |
| (EtO)$_2$Si(CH$_2$)$_3$SH, | [(C$_{14}$H$_{29}$O—(CH$_2$—CH$_2$O)$_3$] |
| (EtO)$_2$Si(CH$_2$)$_3$SH, | [(C$_{14}$H$_{29}$O—(CH$_2$—CH$_2$O)$_4$] |
| (EtO)$_2$Si(CH$_2$)$_3$SH, | [(C$_{14}$H$_{29}$O—(CH$_2$—CH$_2$O)$_5$] |
| (EtO)$_2$Si(CH$_2$)$_3$SH, | [(C$_{14}$H$_{29}$O—(CH$_2$—CH$_2$O)$_6$] |
| (EtO)$_2$Si(CH$_2$)$_3$SH, | [(C$_9$H$_{19}$O—(CH$_2$—CH$_2$O)$_2$]$_2$ |
| (EtO)Si(CH$_2$)$_3$SH, | [(C$_9$H$_{19}$O—(CH$_2$—CH$_2$O)$_3$]$_2$(EtO)Si(CH$_2$)$_3$SH, |
| (CH$_2$)$_3$SH, | [(C$_9$H$_{19}$O—(CH$_2$—CH$_2$O)$_4$]$_2$(EtO)Si |
| (CH$_2$)$_3$SH, | [(C$_9$H$_{19}$O—(CH$_2$—CH$_2$O)$_5$]$_2$(EtO)Si |
| (CH$_2$)$_3$SH, | [(C$_9$H$_{19}$O—(CH$_2$—CH$_2$O)$_6$]$_2$(EtO)Si |
| (CH$_2$)$_3$SH, | [(C$_{12}$H$_{25}$O—(CH$_2$—CH$_2$O)$_2$]$_2$(EtO)Si |
| (CH$_2$)$_3$SH, | [(C$_{12}$H$_{25}$O—(CH$_2$—CH$_2$O)$_3$]$_2$(EtO)Si |
| (CH$_2$)$_3$SH, | [(C$_{12}$H$_{25}$O—(CH$_2$—CH$_2$O)$_4$]$_2$(EtO)Si |
| (CH$_2$)$_3$SH, | [(C$_{12}$H$_{25}$O—(CH$_2$—CH$_2$O)$_5$]$_2$(EtO)Si |
| (CH$_2$)$_3$SH, | [(C$_{12}$H$_{25}$O—(CH$_2$—CH$_2$O)$_6$]$_2$(EtO)Si |
| (CH$_2$)$_3$SH, | [(C$_{13}$H$_{27}$O—(CH$_2$—CH$_2$O)$_2$]$_2$(EtO)Si |
| (CH$_2$)$_3$SH, | [(C$_{13}$H$_{27}$O—(CH$_2$—CH$_2$O)$_3$]$_2$(EtO)Si |
| (CH$_2$)$_3$SH, | [(C$_{13}$H$_{27}$O—(CH$_2$—CH$_2$O)$_4$]$_2$(EtO)Si |
| (CH$_2$)$_3$SH, | [(C$_{13}$H$_{27}$O—(CH$_2$—CH$_2$O)$_5$]$_2$(EtO)Si |
| (CH$_2$)$_3$SH, | [(C$_{13}$H$_{27}$O—(CH$_2$—CH$_2$O)$_6$]$_2$(EtO)Si |
| (CH$_2$)$_3$SH, | [(C$_{14}$H$_{29}$O—(CH$_2$—CH$_2$O)$_2$]$_2$(EtO)Si |
| (CH$_2$)$_3$SH, | [(C$_{14}$H$_{29}$O—(CH$_2$—CH$_2$O)$_3$]$_2$(EtO)Si |
| (CH$_2$)$_3$SH, | [(C$_{14}$H$_{29}$O—(CH$_2$—CH$_2$O)$_4$]$_2$(EtO)Si |
| (CH$_2$)$_3$SH, | [(C$_{14}$H$_{29}$O—(CH$_2$—CH$_2$O)$_5$]$_2$(EtO)Si |
| (CH$_2$)$_3$SH, | [(C$_{14}$H$_{29}$O—(CH$_2$—CH$_2$O)$_6$]$_2$(EtO)Si |
| (CH$_2$)$_3$SH, | [(C$_9$H$_{19}$O—(CH$_2$—CH$_2$O)$_2$]$_3$Si(CH$_2$)$_3$SH, |
| | [(C$_9$H$_{19}$O—(CH$_2$—CH$_2$O)$_3$]$_3$Si(CH$_2$)$_3$SH, |
| | [(C$_9$H$_{19}$O—(CH$_2$—CH$_2$O)$_4$]$_3$Si(CH$_2$)$_3$SH, |
| | [(C$_9$H$_{19}$O—(CH$_2$—CH$_2$O)$_5$]$_3$Si(CH$_2$)$_3$SH, |
| | [(C$_9$H$_{19}$O—(CH$_2$—CH$_2$O)$_6$]$_3$Si(CH$_2$)$_3$SH, |
| | [(C$_{12}$H$_{25}$O—(CH$_2$—CH$_2$O)$_2$]$_3$Si(CH$_2$)$_3$SH, |
| | [(C$_{12}$H$_{25}$O—(CH$_2$—CH$_2$O)$_3$]$_3$Si(CH$_2$)$_3$SH, |
| | [(C$_{12}$H$_{25}$O—(CH$_2$—CH$_2$O)$_4$]$_3$Si(CH$_2$)$_3$SH, |
| | [(C$_{12}$H$_{25}$O—(CH$_2$—CH$_2$O)$_5$]$_3$Si(CH$_2$)$_3$SH, |
| | [(C$_{12}$H$_{25}$O—(CH$_2$—CH$_2$O)$_6$]$_3$Si(CH$_2$)$_3$SH, |
| | [(C$_{13}$H$_{27}$O—(CH$_2$—CH$_2$O)$_2$]$_3$Si(CH$_2$)$_3$SH, |
| | [(C$_{13}$H$_{27}$O—(CH$_2$—CH$_2$O)$_3$]$_3$Si(CH$_2$)$_3$SH, |
| | [(C$_{13}$H$_{27}$O—(CH$_2$—CH$_2$O)$_4$]$_3$Si(CH$_2$)$_3$SH, |
| | [(C$_{13}$H$_{27}$O—(CH$_2$—CH$_2$O)$_5$]$_3$Si(CH$_2$)$_3$SH, |
| | [(C$_{13}$H$_{27}$O—(CH$_2$—CH$_2$O)$_6$]$_3$Si(CH$_2$)$_3$SH, |
| | [(C$_{14}$H$_{29}$O—(CH$_2$—CH$_2$O)$_2$]$_3$Si(CH$_2$)$_3$SH, |
| | [(C$_{14}$H$_{29}$O—(CH$_2$—CH$_2$O)$_3$]$_3$Si(CH$_2$)$_3$SH, |
| | [(C$_{14}$H$_{29}$O—(CH$_2$—CH$_2$O)$_4$]$_3$Si(CH$_2$)$_3$SH, |
| | [(C$_{14}$H$_{29}$O—(CH$_2$—CH$_2$O)$_5$]$_3$Si(CH$_2$)$_3$SH, |
| | [(C$_{14}$H$_{29}$O—(CH$_2$—CH$_2$O)$_6$]$_3$Si(CH$_2$)$_3$SH, and |
| | HS—CH$_2$—CH$_2$—CH$_2$—Si(OCH$_2$—CH$_2$—)$_3$N. |

19. The process for preparing mercaptoorganyl(alkoxysilanes) of claim 18, wherein said hydrogenation is carried out at a temperature of between 100 and 175° C.; under a hydrogen pressure of 5 to 55 bar and wherein the amount of doping component, based on the weight of the doped metal catalyst, is 0.01%-7.5% by weight.

20. The process for preparing mercaptoorganyl(alkoxysilanes) of claim 19, wherein said process is carried out in a reaction mixture containing an additive selected from the group consisting of: a titanium alkoxylate; an amine; water; and an organic or inorganic acid or base.

* * * * *